United States Patent
Vu et al.

(10) Patent No.: US 7,420,079 B2
(45) Date of Patent: Sep. 2, 2008

(54) METHODS AND COMPOUNDS FOR PRODUCING DIPEPTIDYL PEPTIDASE IV INHIBITORS AND INTERMEDIATES THEREOF

(75) Inventors: Truc Chi Vu, Watchung, NJ (US); David B. Brzozowski, Island Lake, IL (US); Rita Fox, Princeton, NJ (US); Jollie Duaine Godfrey, Jr., Ewing, NJ (US); Ronald L. Hanson, Morris Plains, NJ (US); Sergei V. Kolotuchin, Roselle Park, NJ (US); John A. Mazzullo, Florence, SC (US); Ramesh N. Patel, Bridgewater, NJ (US); Jianji Wang, Dayton, NJ (US); Kwok Wong, Lawrenceville, NJ (US); Jurong Yu, Dayton, NJ (US); Jason J. Zhu, East Brunswick, NJ (US); David R. Magnin, Hamilton, NJ (US); David J. Augeri, Princeton, NJ (US); Lawrence G. Hamann, Cherry Hill, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 369 days.

(21) Appl. No.: 10/716,012

(22) Filed: Nov. 18, 2003

(65) Prior Publication Data

US 2005/0090539 A1   Apr. 28, 2005

Related U.S. Application Data

(60) Provisional application No. 60/431,814, filed on Dec. 9, 2002.

(51) Int. Cl.
   *C07C 69/52* (2006.01)
   *C07C 229/02* (2006.01)
(52) U.S. Cl. .................. 560/155; 560/174; 560/189
(58) Field of Classification Search .................. 560/174, 560/189, 155, 115
   See application file for complete search history.

(56) References Cited

U.S. PATENT DOCUMENTS 3,325,478 A * 6/1967 Hermann et al. ............ 540/331
6,068,991 A   5/2000 Liu et al.
6,395,767 B2  5/2002 Robl et al.

FOREIGN PATENT DOCUMENTS

| EP | 0 808 824 | 11/1997 |
|----|-----------|---------|
| WO | WO 00/04179 | 1/2000 |
| WO | WO2004/037181 | 5/2004 |
| WO | WO2005/012249 | 2/2005 |
| WO | WO2005/049022 | 6/2005 |

OTHER PUBLICATIONS

Hanessian, S. et al., "Probing the Importance of Spacial and Conformational Domains in Captopril Analogs for Angiotensin Converting Enzyme Activity", Bioorganic & Medicinal Chemistry Letters, vol. 8, pp. 2123-2128 (1998).
Hanson, R.L. et al., Synthesis of allysine ethylene acetal using phenylalanine dehydrogenase from *Thermoactinomyces intermedius*, Enzyme and Microbial Technology, vol. 26, pp. 348-358 (2000).
Imashiro, R. et al., "Asymmetric synthesis of methyl (2*R*,3*S*)-3-(4-methoxyphenyl) glycidate, a key intermediate of diltiazem, via Mukaiyama aldol reaction", Tetrahedron Letters, vol. 42, pp. 1313-1315 (2001).
Reetz, M.T. et al., "General Synthesis of Potentially Antiviral α-Adamantyl Carbonyl Compounds", Angew. Chem. Int. Ed. Engl., vol. 18, No. 1, p. 72 (1979).
Sagnard, I. et al., "Enantioselective Synthesis of Cyclopropane α-Amino Acids: Synthesis of N-Boc-*cis*-(2S,3R,4S)-3,4-Methanoproline and N-Boc-(2S,3R,4S)-3,4-Methanoglutamic Acid", Tetrahedron Letters, vol. 36, No. 18, pp. 3148-3152 (1995).
Takada, H. et al., "Thermostable Phenylalanine Dehydrogenase of *Thermoactinomyces intermedius*: Cloning, Expression, and Sequencing of Its Gene", J. Biochem., vol. 109, pp. 371-376 (1991).
Tverezovsky, V.V. et al., "Synthesis of (2S,3R, 4S)-3,4-Methanoproline and Analogues by Cyclopropylidene Insertion", Tetrahedron, vol. 53, No. 43, pp. 14773-14792 (1997).
U.S. Appl. No. 11/091,183, filed Mar. 28, 2005, Sharma et al.
U.S. Appl. No. 11/104,015, filed Apr. 12, 2005, Politino et al.
U.S. Appl. No. 11/119,552, filed May 2, 2005, Patel et al.
U.S. Appl. No. 11/135,217, filed May 23, 2005, Sharma.
Bott, et al., "Synthesis of alpha.-chloro-1-adamantylacetic acids and. alpha.-chloro-2-norbornaneacetic acid by means of trichloroethylene", Chemical Abstracts, Accession No. 1968:21595, (1967).
Clariana, J. et al, "Preparation of (R)-(1-adamantyl)glycine and (R)-2-(1-adamantyl)-2-aminoethanol: a combination of cobalt-mediated β-ketoester alkylation and enzyme-based aminoalcohol resolution", Tetrahedron: Asymmetry 11, 2000, pp. 4549-4557.
Janku, J. et al., "Adamantane and its derivatives. XXXIV. Preparation of 1-adamantylchloroacetic acid", Chemical Abstracts, Accession No. 1976:105072, (1973).
Kottirsch, G., et al., "Fibrinogen receptor antagonists containing a gamma-lactam Gly-Asp isosters", Database Accession No. 120:299271, Bioorganic & Medicinal Chemistry Letters, 3(8), 1993.
Kranyushkin, M. et al., "Synthesis and properties of .alpha.-c-nitrohydrazones. 3. Interaction of salts of asymmetric hydrazines with compounds containing trinitromethyl groups and with polynitromethanes", Database Accession No. 1980:494874, (1980).

(Continued)

*Primary Examiner*—Rebecca L Anderson
*Assistant Examiner*—Shawquia Young
(74) *Attorney, Agent, or Firm*—McDonnell Boehnen Hulbert & Berghoff

(57) ABSTRACT

Methods and compounds for production of cyclopropyl-fused pyrrolidine-based inhibitors of dipeptidyl peptidase IV are provided.

6 Claims, No Drawings

OTHER PUBLICATIONS

Krasutskii, P.A. et al., "Synthesis and chemical characteristics of .alpha.-halo(1-adamantyl)acetyl halides", Chemical Abstracts, Accession No. 1985:422196, (1984).

Krasutskii, P.A. et al., "alpha.-Amino acids of the adamantine series, II. Synthesis and isomer separation of 1,3-adamantane diglycine. Stereo-chemistry of amination of .alpha.-bromo acids of the adamantane series", Accession No. 1986: 625851, (1985).

Krasutskii, P.A. et al., "Amino acids of the adamantane series. I. Synthesis and antiviral activity of adamantane .alpha.-amino acids and their derivatives", Accession No. 1986:130230, (1985).

Krasutskii, P.A. et al., ".alpha.-Amino acids of the adamantane series. I. Synthesis and resolution of -adamantylglycine and .beta.-(1-adamantyl)alanine", Accession No. 1986: 406210 (1985).

Ohno, M. et al., "Ethyl 3-(1-Adamantyl)-2-diazo-3-oxopropanoate: Synthetic Use of the Preparation of Some Adamantane Derivatives", Synthesis (8), pp. 793-796, 1993.

Stetter, H. et al. "Compounds with urotropine structure. XVI. The chemistry of 1-adamantyl derivatives", Chemische Berichte, 93, 226-230, (1960).

Yurchenko, A.G. et al, ".alpha. -Amino-1-adamantaneacetic acid", Accession No. 1982: 472778 (Mar. 1982).

* cited by examiner

SEQUENCE LISTING

<160> NUMBER OF SEQ ID NOS: 8

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide

<400> SEQUENCE: 1
tcgtcatgaa aatcgttctc gttttg                                           26

<210> SEQ ID NO 2
<211> LENGTH: 28
<212> TYPE: DNA
<213> ORGANISM: Artificial
<220> FEATURE:
<223> OTHER INFORMATION: Synthetic oligonucleotide

<400> SEQUENCE: 2
tactgttttt ccagcgtatt cctaggct                                         28

<210> SEQ ID NO 3
<211> LENGTH: 33
<212> TYPE: DNA
<213> ORGANISM: Artificial
<220> FEATURE:
<223> OTHER INFORMATION: Synthetic oligonucleotide

<400> SEQUENCE: 3
gatgctcata tgcgcgacgt gtttgaaatg atg                                   33

<210> SEQ ID NO 4
<211> LENGTH: 30
<212> TYPE: DNA
<213> ORGANISM: Artificial
<220> FEATURE:
<223> OTHER INFORMATION: Synthetic oligonucleotide

<400> SEQUENCE: 4
gatcccgggc taaggcgaat taataattcg                                       30

<210> SEQ ID NO 5
<211> LENGTH: 18
<212> TYPE: DNA
<213> ORGANISM: Thermoactinomycetes intermedius

<400> SEQUENCE: 5
aacagcgcaa ggaggtaa                                                    18

<210> SEQ ID NO 6

```
<211> LENGTH: 5
<212> TYPE: PRT
<213> ORGANISM: Thermoactinomycetes intermedius

<400> SEQUENCE: 6

Asn Ser Ala Arg Arg
1               5

<210> SEQ ID NO 7
<211> LENGTH: 54
<212> TYPE: DNA
<213> ORGANISM: Artificial
<220> FEATURE:
<223> OTHER INFORMATION: Modified phenylalanine dehydrogenase from
      Thermoactinomycetes intermedius

<400> SEQUENCE: 7
aacagcgcgg aggggtacct cgagccgcgg cggccgcgaa ttaattcgcc ttag        54

<210> SEQ ID NO 8
<211> LENGTH: 17
<212> TYPE: PRT
<213> ORGANISM: Artificial
<220> FEATURE:
<223> OTHER INFORMATION: Modified phenylalanine dehydrogenase from
      Thermoactinomycetes intermedius

<400> SEQUENCE: 8

Asn Ser Ala Glu Gly Tyr Leu Glu Pro Arg Arg Pro Arg Ile Asn Ser
1               5                   10                  15
Pro
```

METHODS AND COMPOUNDS FOR PRODUCING DIPEPTIDYL PEPTIDASE IV INHIBITORS AND INTERMEDIATES THEREOF

This application claims priority from U.S. Provisional Application 60/431,814 filed Dec. 9, 2002 which is incorporated herein by reference.

FIELD OF THE INVENTION

The present invention provides methods and compounds for use in methods for production of cyclopropyl-fused pyrrolidine-based inhibitors of dipeptidyl peptidase IV. Also provided are methods for asymmetric reductive amination of the intermediate compound (S)-amino-(3-hydroxy-adamantan-1-yl)-acetic acid used in the production of cyclopropyl-fused pyrrolidine-based inhibitors of dipeptidyl peptidase IV. Additional intermediate compounds and methods for their production are also provided. Dipeptidyl peptidase IV inhibitors produced by the compounds and methods of the present invention are useful in the treatment of diabetes and complications thereof, hyperglycemia, Syndrome X, hyperinsulinemia, obesity, and atherosclerosis and related diseases, as well as immunomodulatory diseases and chronic inflammatory bowel disease.

BACKGROUND OF THE INVENTION

Dipeptidyl peptidase IV is a membrane bound non-classical serine aminopeptidase which is located in a variety of tissues including, but not limited to, intestine, liver, lung, and kidney. This enzyme is also located on circulating T-lymphocytes wherein it is referred to as CD-26. Dipeptidyl peptidase IV is responsible for the metabolic cleavage of the endogenous peptides GLP-1(7-36) and glucagons in vivo and has demonstrated proteolytic activity against other peptides such as GHRH, NPY, GLP-2 and VIP in vitro.

GLP-1(7-36) is a 29 amino acid peptide derived from post-translational processing of proglucagon in the small intestine. This peptide has multiple actions in vivo. For example, GLP-1(7-36) stimulates insulin secretion and inhibits glucagon secretion. This peptide promotes satiety and slows gastric emptying. Exogenous administration of GLP-1(7-36) via continuous infusion has been shown to be efficacious in diabetic patients. However, the exogenous peptide is degraded too rapidly for continual therapeutic use.

Inhibitors of dipeptidyl peptidase IV have been developed to potentiate endogenous levels of GLP-1(7,36). U.S. Pat. No. 6,395,767 discloses cyclopropyl-fused pyrrolidine-based inhibitors of dipeptidyl peptidase IV. Methods for chemically synthesizing these inhibitors are disclosed in U.S. Pat. No. 6,395,767 as well as in the literature. For example, see Sagnard et al. Tet-Lett. 1995 36:3148-3152; Tverezovsky et al. Tetrahedron 1997 53:14773-14792; and Hanessian et al. Bioorg. Med. Chem. Lett. 1998 8:2123-2128. A preferred inhibitor disclosed in U.S. Pat. No. 6,395,767 is the free base, (1S, 3S,5S)-2-[(2S)-2-amino-2-(3-hydroxy-tricyclo[3.3.1.1$^{3,7}$]dec-1-yl)-1-oxoethyl]-2-azabicyclo-[3.1.0]hexane-3-carbonitrile (M').

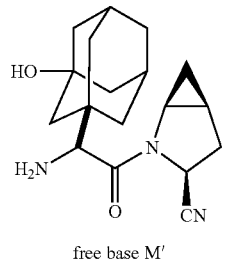

free base M'

Methods adapted for preparing intermediates used in the production of this dipeptidyl peptidase IV inhibitor are disclosed in EP 0 808 824 A2. Also see, Imashiro and Kuroda Tetrahedron Letters 2001 42:1313-1315, Reetz et al. Chem. Int. Ed. Engl. 1979 18:72, Reetz and Heimbach Chem. Ber. 1983 116:3702-3707, Reetz et al. Chem. Ber. 1983 116:3708-3724.

The present invention provides new production methods and compounds for use in the production of cyclopropyl-fused pyrrolidine-based inhibitors of dipeptidyl peptidase IV.

SUMMARY OF THE INVENTION

An object of the present invention is to provide compounds useful as intermediates in the production of cyclopropyl-fused pyrrolidine-based inhibitors of dipeptidyl peptidase IV.

In one embodiment, intermediates of the present invention comprise a compound of Formula IA:

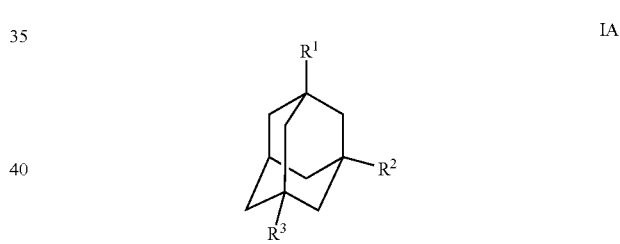

wherein
$R^1$ is selected from the group consisting of H and OH;
$R^2$ is selected from the group consisting of —C(=O)—COR$^4$, —C(=O)NR$^5$R6, —C(X)$_n$—COR$^4$ and

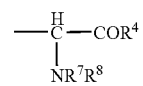

wherein
X is a halogen;
n is from 1-2
$R^4$ is selected from the group consisting of O-alkyl, NH$_2$ and OH; and
$R^5$, $R_6$, $R_7$ and $R^8$ are each selected from the group consisting of H and COOR$^9$, wherein R$^9$ is a substituted or unsubstituted alkyl; and
$R^3$ is selected from the group consisting of H, OH and R$^{10}$, wherein R$^{10}$ is NHR$^{11}$C(=O)R
$R^{11}$ is R$^{13}$COOH,
$R^{12}$ is

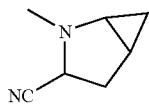

and $R^{13}$ is an alkyl or aryl.

Exemplary preferred compounds of Formula IA of the present invention useful as intermediates in the production of cyclopropyl-fused pyrrolidine-based inhibitors of dipeptidyl peptidase IV include:

3-hydroxy-α-oxotricyclo[3.3.1.1$^{3,7}$]decane-1-acetic acid, methyl ester as depicted in Formula I,

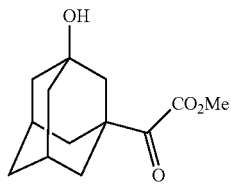

I 3-hydroxy-α-oxotricyclo[3.3.1.1$^{3,7}$]decane-1-acetic acid as depicted in Formula II,

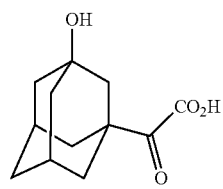

II (αS)-α-amino-3-hydroxytricyclo[3.3.1.1$^{3,7}$]decane-1-acetic acid as depicted in Formula V,

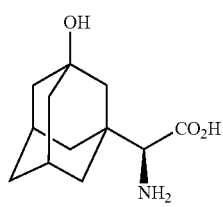

V (αS)-α-[[(1,1-dimethylethoxy)carbonyl]amino]-3-hydroxytricyclo[3.3.1.1$^{3,7}$]decane-1-acetic acid as depicted in Formula VI,

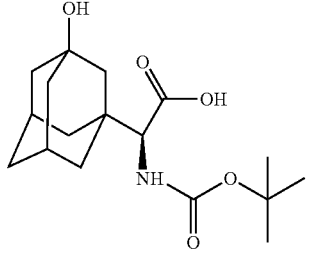

VI (or its DABCO salt VIA), adamantan-1-yl-dichloro-acetic acid methyl ester as depicted in Formula VII,

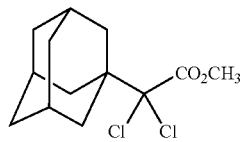

VII dichloro-(3-hydroxy-adamantan-1-yl)-acetic acid methyl ester as depicted in Formula VIII, and

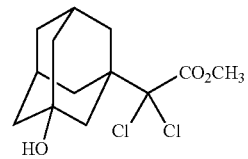

VIII dichloro-(3-hydroxy-adamantan-1-yl)-acetic acid as depicted in Formula IX

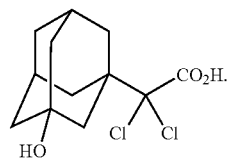

IX

In another embodiment, intermediates of the present invention comprise the compounds 4,5-dihydro-1H-pyrrole-1,5-dicarboxylic acid, 1-(1,1-dimethylethyl),5-ethyl ester as depicted in Formula III,

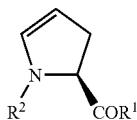

wherein

R[1] is selected from the group consisting of O-alkyl, NH$_2$ and OH, and

R[2] is selected from the group consisting of t-BOC and CBz;

and (5S)-5-aminocarbonyl-4,5-dihydro-1H-pyrrole-1-carboxylic acid, 1-(1,1-dimethylethyl)ester as depicted in Formula IV,

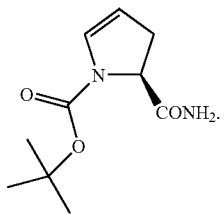

In a preferred embodiment, these compounds are used as intermediates in the production of the dipeptidyl peptidase IV inhibitors (1S,3S,5S)-2-[(2S)-2-amino-2-(3-hydroxytricyclo [3.3.1.1$^{3,7}$]dec-1-yl)-1-oxoethyl]-2-azabicyclo[3.1.0]hexane-3-carbonitrile, benzoate (1:1) as depicted in Formula M

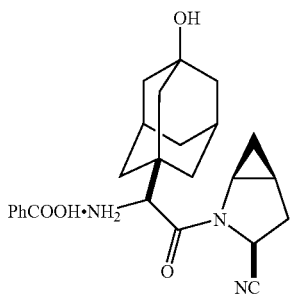

or its free base M' (set out above), and monohydrate M" thereof

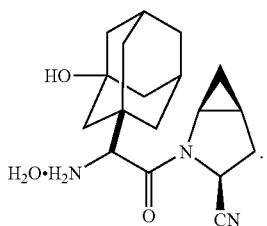

Another object of the present invention is to provide methods for production of cyclopropyl-fused pyrrolidine-based inhibitors of dipeptidyl peptidase IV. In a preferred embodiment, the inhibitor produced are (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) and its corresponding free base as depicted in Formulas M and M', respectively. These inhibitors are ultimately formed from the coupling of two fragments, (<aS)-<a-amino-3-hydroxytricyclo[3.3.1.1$^{3,7}$]decane-1-acetic acid as depicted in Formula V,

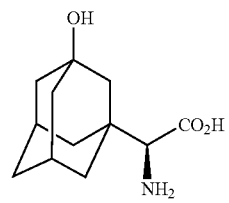

and (1S,3S,5S)-2-azabicyclo[3.1.0]hexane-3-carboxamide acid salt such as the hydrochloride salt or the methanesulfonic acid salt (mesyl or MSA salt) as depicted in Formula J

Various methods are disclosed herein for production and coupling of these fragments depending upon the intermediate compounds selected as the starting materials. For example, in one embodiment of the present invention, a method is provided for production of the cyclopropyl-fused pyrrolidine-based inhibitor from 3-hydroxy-<a-oxotricyclo[3.3.1.1$^{3,7}$] decane-1-acetic acid as depicted in Formula II. In another embodiment of the present invention, a method is provided for production of the cyclopropyl-fused pyrrolidine-based inhibitor from (<aS)-<a-amino-3-hydroxytricyclo[3.3.1.1$^{3,7}$] decane-1-acetic acid of Formula V. In another embodiment of the present invention, a method is provided for production of the cyclopropyl-fused pyrrolidine-based inhibitor from (<aS)-<a[[(1,1-dimethylethoxy)carbonyl]amino]-3-hydroxytricyclo[3.3.1.1$^{3,7}$]decane-1-acetic acid of Formula VI. In yet another embodiment of the present invention, a method is provided for production of the cyclopropyl-fused pyrrolidine-based inhibitor from (5S)-5-aminocarbonyl-4,5-dihydro-1H-pyrrole-1-carboxylic acid, 1-(1,1-dimethylethyl) ester of Formula IV.

Another object of the present invention is to provide methods for synthesis of intermediates useful in the production of cyclopropyl-fused pyrrolidine-based inhibitor. In one embodiment of the present invention, a method is provided for asymmetric reductive amination or transamination of 3-hydroxy-<a-oxotricyclo[3.3.1.1$^{3,7}$]decane-1-acetic acid (Formula II) to (<aS)-<a-amino-3-hydroxytricyclo[3.3.1.1$^{3,}$ $^7$]decane-1-acetic acid (Formula V). In another embodiment of the present invention, a method for chemical synthesis of (<aS)-<a-amino-3-hydroxytricyclo[3.3.1.1$^{3,7}$]decane-1-acetic acid (Formula V) from tricyclo[3.3.1.1$^{3,7}$]decane-1-acetic acid (Formula N) is provided. In another embodiment of the present invention, methods are provided for production of 3-hydroxy-<a-oxotricyclo[3.3.1.1 $^{3,7}$]decane-1-acetic acid (Formula II) from adamantan-1-yl-dichloro-acetic acid methyl ester (Formula VII), dichloro-(3-hydroxy-adamantan-1-yl)-acetic acid methyl ester (Formula VIII), and dichloro-(3-hydroxy-adamantan-1-yl)-acetic acid (Formula IX). Methods for production of adamantan-1-yl-dichloro-acetic acid methyl ester (Formula VII), dichloro-(3-hydroxy-adamantan-1-yl)-acetic acid methyl ester (Formula VIII), and dichloro-(3-hydroxy-adamantan-1-yl)-acetic acid (Formula IX) are also provided. In another embodiment of the present invention, a method is provided for production of (5S)-5-aminocarbonyl-4,5-dihydro-1H-pyrrole-1-carboxylic acid, 1-(1,1-dimethylethyl) ester (Formula IV) from 4,5-dihydro-1H-pyrrole-1,5-dicarboxylic acid, 1-(1,1-dimethylethyl),5-ethyl ester (Formula III). In this embodiment, (5S)-5-aminocarbonyl-4,5-dihydro-1H-pyrrole-1-carboxylic acid, 1-(1,1-dimethylethyl)ester (Formula (IV) can then be used as an intermediate in the production of [1S-(1<a,3<b,5<a]-3-aminocarbonyl)-2-azabicyclo[3.1.0]hexane-2-carboxylic acid, 1,1-dimethylethyl ester (Formula H).

Another object of the present invention is to provide a cell line capable of producing (<aS)-<a-amino-3-hydroxytricyclo[3.3.1.1$^{3,7}$]decane-1-acetic acid (Formula V) by asymmetric reductive amination or transamination of 3-hydroxy-<a-oxotricyclo[3.3.1.1$^{3,7}$]decane-1-acetic acid (Formula II). In a preferred embodiment, the cell line comprises cells containing a plasmid expressing formate dehydrogenase and phenylalanine dehydrogenase. Most preferred is the cell line of ATCC Accession Number PTA-4520.

DETAILED DESCRIPTION OF THE INVENTION

Cyclopropyl-fused pyrrolidine-based compounds such as (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) and its corresponding free base and monohydrate thereof are dipeptidyl peptidase IV inhibitors useful in the treatment of diabetes and complications thereof, hyperglycemia, Syndrome X, hyperinsulinemia, obesity, and atherosclerosis and related diseases, as well as immunomodulatory diseases and chronic inflammatory bowel disease. In the present invention, new compounds and methods are provided for use in production of cyclopropyl-fused pyrrolidine-based compounds such as (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) and its corresponding free base and monohydrate thereof.

The dipeptidyl peptidase IV inhibitors (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) is depicted below as Formula M.

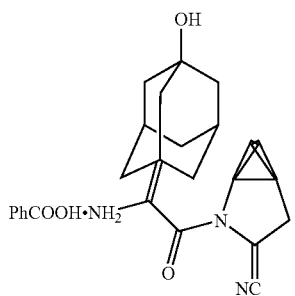

M and preferably the corresponding free base Formula M' depicted below or its monohydrate M" set out hereinbefore.

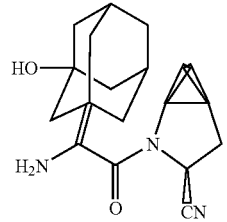

M'

In the present invention, a method is provided for production of (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile (Formula M') by assembly of two fragments. These fragments are (<aS)-<a-amino-3-hydroxytricyclo[3.3.1.1$^{3,7}$]decane-1-acetic acid as depicted in Formula V,

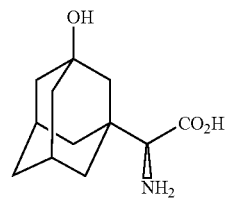

V and acid salts of (1S,3S,5S)-2-azabicyclo[3.1.0]hexane-3-carboxamide such as the hydrochloride salt or MSA salt as depicted in Formula J.

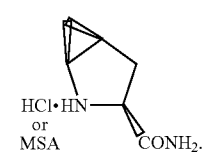

J

The present invention also provides methods for production of these fragments as well as intermediate compounds useful in the production of these fragments.

In one aspect of the present invention, methods are provided for production of the fragment (<aS)-<a-amino-3-hydroxytricyclo[3.3.1.1$^{3,7}$]decane-1-acetic acid (Formula V) by reductive amination or transamination of the intermediate compound 3-hydroxy-<a-oxotricyclo[3.3.1.1$^{3,7}$]decane-1-acetic acid (Formula II). In a preferred embodiment of this method, 3-hydroxy-<a-oxotricyclo[3.3.1.1$^{3,7}$]decane-1-acetic acid (Formula II) is converted to (<aS)-<a-amino-3-hydroxytricyclo[3.3.1.1$^{3,7}$]decane-1-acetic acid (Formula V) by reductive amination performed enzymatically using a phenylalanine dehydrogenase or other amino acid dehydrogenases active with ketoacids. Exemplary phenylalanine dehydrogenases useful in the present invention include, but are not limited to, those from *Sporosarcina* species or a phenylalanine dehydrogenase from *Thermoactinomyces* species such as *Thermoactinomyces intermedius*. It is preferred that reductive amination be performed with the phenylalanine dehydrogenase of *Thermoactinomyces intermedius*, ATCC 33205, expressed in *Escherichia coli* or *Pichia pastoris*. Construction and growth of recombinant strains of *E. coli* and *Pichia pastoris* expressing phenylalanine dehydrogenase *Thermoactinomyces intermedius*, ATCC 33205, have been described by Hanson et al. (Enzyme and Microbial Technology 2000 26:348-358). Growth of *Pichia pastoris* on methanol also induces the production of formate dehydrogenase (Hanson et al. Enzyme and Microbial Technology 2000 26:348-358).

*E. coli* cells containing a plasmid expressing the *Pichia pastoris* (ATCC 20864) formate dehydrogenase and a modified version of the *Thermoactinomyces intermedius* (ATCC 33205) phenylalanine dehydrogenase gene were deposited and accepted by an International Depository Authority under the provisions of the Budapest Treaty. The deposit was made on Jun. 25, 2002 to the American Type Culture Collection at 10801 University Boulevard in Manassas, Va. 20110-2209. The ATCC Accession Number is PTA-4520. All restrictions upon public access to this cell line will be irrevocably removed upon granting of this patent application. The Deposit will be maintained in a public depository for a period of thirty years after the date of deposit or five years after the last request for a sample or for the enforceable life of the patent, whichever is longer. The above-referenced cell line was viable at the time of the deposit. The Deposit will be replaced if viable samples cannot be dispensed by the depository.

Reductive amination of 3-hydroxy-<aS-a-oxotricyclo[3.3.1.1$^{3,7}$]decane-1-acetic acid (Formula II) to (<aS)-<a-amino-3-hydroxytricyclo[3.3.1.1$^{3,7}$]decane-1-acetic acid (Formula V) is depicted in the following Scheme I.

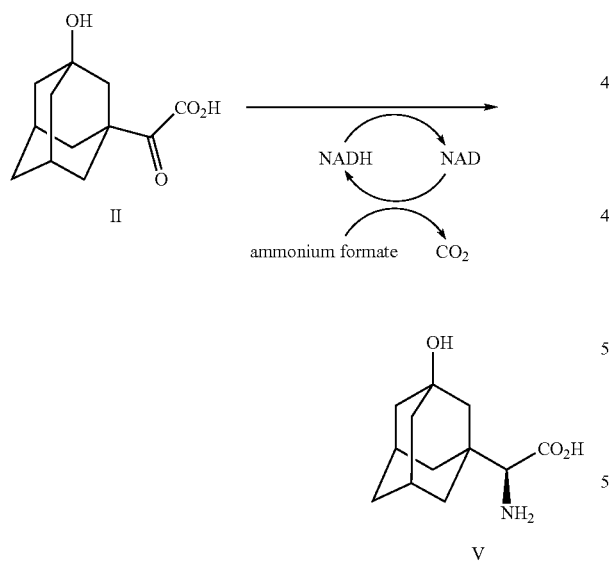

As shown in Scheme I, this reaction requires ammonia and reduced nicotinamide adenine dinucleotide (NADH). Nicotinamide adenine dinucleotide (AND) produced during the reaction is recycled to NADH by the oxidation of formate to carbon dioxide by formate dehydrogenase. The expected yield of (<aS)-<a-amino-3-hydroxytricyclo[3.3.1.1$^{3,7}$]decane-1-acetic acid (Formula V) from this reaction is 80 to 100% and the expected enantiomeric excess is greater than 99%. Also see Examples 1 through 10 herein.

The same conversion can also be accomplished using a transaminase as shown in Scheme II:

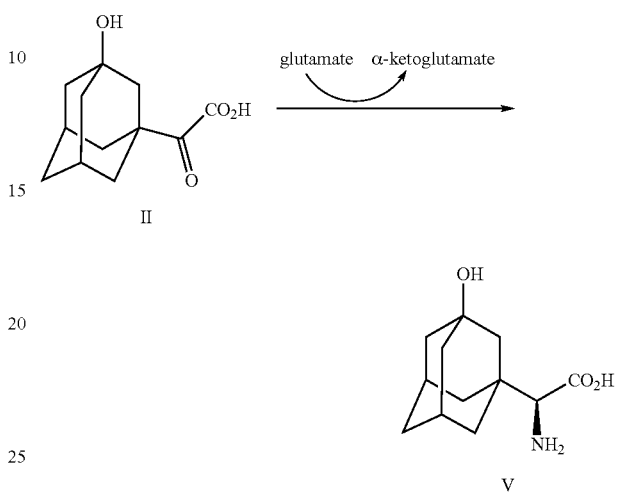

As shown in Scheme II, in this enzymatic conversion glutamic acid serves as the amino donor. An exemplary transaminase for use in this conversion is the branched chain transaminase set forth in Example 11 herein.

In another embodiment, (<aS)-<a-amino-3-hydroxytricyclo[3.3.1.1$^{3,7}$]decane-1-acetic acid (Formula V) is synthesized chemically. An exemplary method for chemical synthesis of (<aS)-<a-amino-3-hydroxytricyclo[3.3.1.13,7]decane-1-acetic acid (Formula V) is depicted in Scheme III:

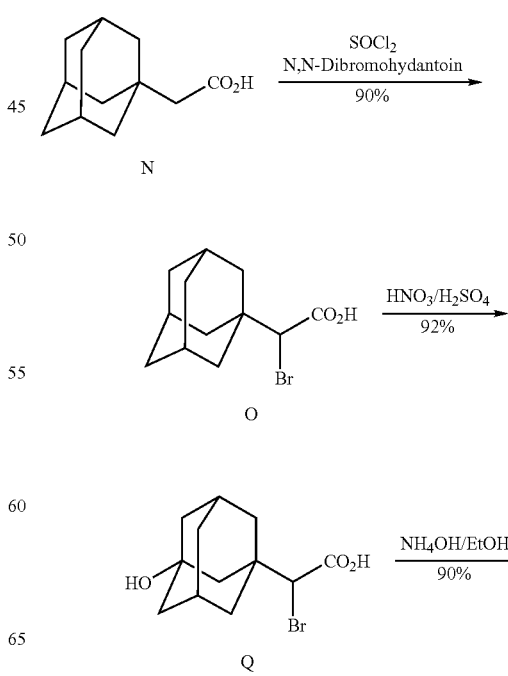

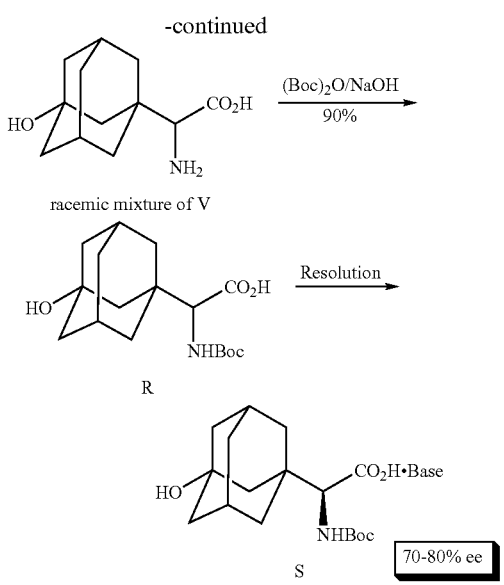

As shown in Scheme III, a racemic mixture of (<aS)-<a-amino-3-hydroxytricyclo[3.3.1.1$^{3,7}$]decane-1-acetic acid (Formula V) is chemically synthesized from tricyclo[3.3.1.1$^{3,7}$]decane-1-acetic acid (Formula N) by first brominating tricyclo[3.3.1.1$^{3,7}$]decane-1-acetic acid into α-bromotricyclo[3.3.1.1$^{3,7}$]decane-1-acetic acid (Formula O). In this bromination, the starting material, tricyclo[3.3.1.1$^{3,7}$]decane-1-acetic acid (Formula N) is suspended in thionyl chloride. Dimethyl formamide (DMF) is then added and the suspension is stirred at room temperature for 1.5 hours. Completion of the reaction is verified by gas chromatography. Solid N-bromosuccinic anhydride (NBS) is then added portionwise to the reaction mixture and the reaction mixture is heated to 60° C. The temperature is maintained between 60 and 65° C. while the reaction is stirred for 3 hours. Again, completion of the reaction is verified by gas chromatography. Heptane is then added to the reaction mixture and excess thionyl chloride is distilled off at 78-80° C. Water is added to quench the reaction and additional heptane is added. The aqueous layer is then separated from the organic layer and the organic layer is washed with water. After washing, additional water is added to the heptane layer and the heptane is distilled off. Tetrahydrofuran (THF) is then added to the remaining aqueous layer and the mixture is stirred vigorously at room temperature for multiple hours. Additional water can be added to speed up this hydrolysis. The THF is then distilled off, leaving a biphasic (water and oil) reaction mixture. Seeds are then added and the reaction is allowed to reach room temperature while α-bromotricyclo[3.3.1.1$^{3,7}$]decane-1-acetic acid (Formula O) is produced as a heavy solid. Water and acetonitrile are added to keep the suspension stirrable. After stirring for several hours, the solid containing α-bromotricyclo[3.3.1.1$^{3,7}$]decane-1-acetic acid (Formula O) is filtered off and washed several times with acetonitrile. See also Example 17 herein.

α-Bromotricyclo[3.3.1.1$^{3,7}$]decane-1-acetic acid (Formula O) is then reacted with $H_2SO_4$ and $HNO_3$ to produce α-bromo-3-hydroxytricyclo[3.3.1.1$^{3,7}$]decane-1-acetic acid (Formula Q). More specifically, α-bromo-3-hydroxytricyclo[3.3.1.1$^{3,7}$]decane-1-acetic acid (Formula Q) is prepared from α-bromotricyclo[3.3.1.1$^{3,7}$]decane-1-acetic acid (Formula O) by first charging an Erlen-Meyer flask with $H_2SO_4$.

The flask is then cooled in an ice bath and 50% $HNO_3$ is added to the flask. The solid α-bromotricyclo[3.3.1.1$^{3,7}$]decane-1-acetic acid (Formula O) is then added to the mixture in portions which maintain the temperature under 28° C. The reaction is then heated to 60° C. with stirring until a clear solution is obtained. When the reaction is complete, it is cooled to and maintained at room temperature. Water is then added to quench the reaction. The resulting slurry is cooled in an ice bath and then filtered to obtain α-bromo-3-hydroxytricyclo [3.3.1.1$^{3,7}$]decane-1-acetic acid (Formula Q). See also Example 18 herein.

α-Bromo-3-hydroxytricyclo[3.3.1.1$^{3,7}$]decane-1-acetic acid (Formula Q) is then dissolved in ammonium hydroxide, preferably 30% ammonium hydroxide and the reaction mixture is heated preferably to 65° C. The reaction mixture is then concentrated to a solid. EtOH is then added and the reaction is again concentrated to yield a racemic mixture comprising (<aS)-<a-amino-3-hydroxytricyclo[3.3.1.1$^{3,7}$]decane-1-acetic acid (Formula V). See also Example 19 herein.

To isolate (<aS)-<a-amino-3-hydroxytricyclo[3.3.1.1$^{3,7}$]decane-1-acetic acid (racemic mixture of Formula V) from the racemic mixture, the mixture is treated by typical Boc protection using Boc anhydride and sodium hydroxide in tetrahydrofuran to yield α-[[(1,1-dimethylethoxy)carbonyl]amino]-]3]hydroxytricyclo[3.3.1.1$^{3,7}$]decane-1-acetic acid (Compound R). α-[[(1,1-Dimethylethoxy)carbonyl]amino]-]3]hydroxytricyclo[3.3.1.1$^{3,7}$]decane-1-acetic acid (Compound R) is then mixed with a chiral base such as [1R,2S]-(−)-1,2-diphenylhydroxy ethylamine, 1,7,7-trimethylbicyclo[2.2.1]heptane-2-amine, or S-(−)-1-1(1-naphthyl) ethylamine and the mixture is evaporated to dryness. The dried mixture is resuspended in a solvent and the resuspended mixture is placed on a shaker with heating for several hours. Upon cooling to room temperature, crystallization of (aS)-α-[[dimethylethoxy)carbonyl]amino]-3-hydroxytricyclo [3.3.1.1$^{3,7}$]decane-1-acetic acid (Compound S) occurs. See also Example 20 herein.

Removal of the Boc group yields (<aS)-<a-amino-3-hydroxytricyclo[3.3.1.1$^{3,7}$]decane-1-acetic acid (Formula V).

Another aspect of the present relates to methods for production of the intermediate compound 3-hydroxy-<a-oxotricyclo[3.3.1.1$^{3,7}$]decane-1-acetic acid (Formula II) used in the synthesis of the fragment (<aS)-<a-amino-3-hydroxytricyclo[3.3.1.1$^{3,7}$]decane-1-acetic acid (Formula V). The intermediate compound 3-hydroxy-<a-oxotricyclo[3.3.1.1$^{3,7}$]decane-1-acetic acid (Formula II) can be produced in accordance with the method depicted in Scheme IV.

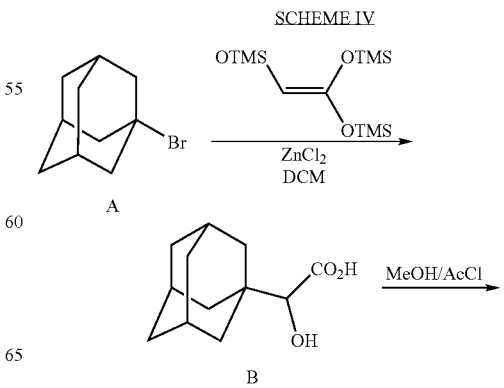

-continued

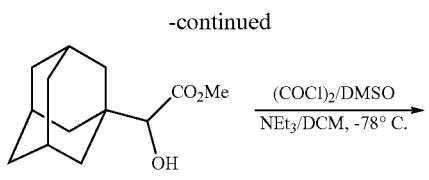

C

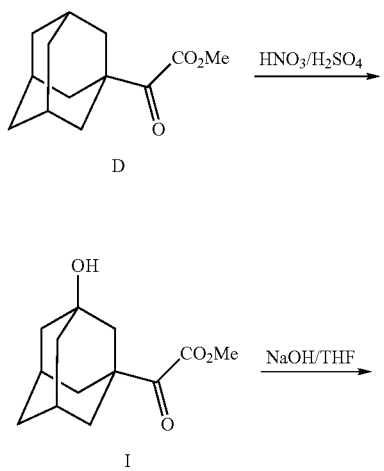

I

-continued

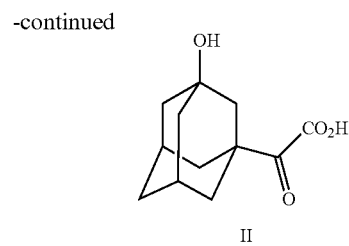

II

As shown in Scheme IV, in this method, adamantyl bromide (Formula A) is alkylated via zinc chloride catalysis to produce <a-hydroxytricyclo[3.3.1.1[3,7]]decane-1-acetic acid (Formula B). <a-Hydroxytricyclo[3.3.1.1[3,7]]decane-1-acetic acid (Formula B) is then esterified using acetyl chloride in methanol to produce <a-hydroxytricyclo[3.3.1.1[3,7]]decane-1-acetic acid, methyl ester (Formula C). <a-Hydroxytricyclo [3.3.1.1[3,7]]decane-1-acetic acid, methyl ester (Formula C) is then converted to <a-oxotricyclo[3.3.1.1[3,7]]decane-1-acetic acid, methyl ester (Formula D) by Swern oxidation. <a-Oxotricyclo[3.3.1.1[3,7]]decane-1-acetic acid, methyl ester (Formula D) is then hydroxylated to form 3-hydroxy-<a-oxotricyclo[3.3.1.1[3,7]]decane-1-acetic acid, methyl ester (Formula I), which is then hydrolyzed to form 3-hydroxy-<a-oxotricyclo[3.3.1.1[3,7]]decane-1-acetic acid (Formula II). Also see Examples 21 through 25 herein.

Alternatively, the intermediate compound 3-hydroxy-<a-oxotricyclo [3.3.1.1[3,7]]decane-1-acetic acid (Formula II) can be produced in accordance with the method depicted in Scheme V.

SCHEME V

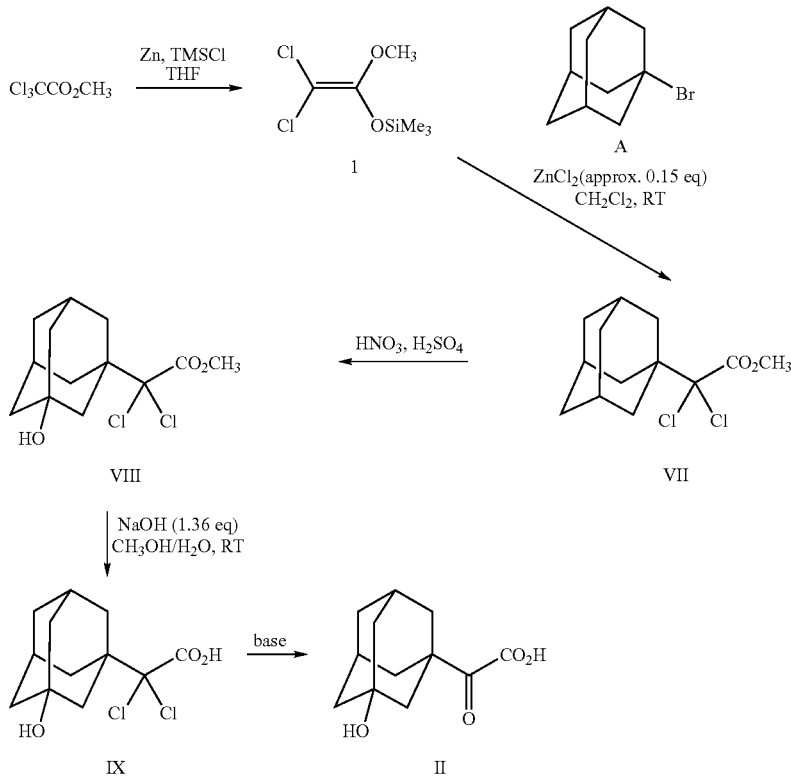

As shown in Scheme V, (2,2-dichloro-1-methoxy-vinyloxy)-trimethysilane 1 is prepared by minor modification of the method of Kuroda et al. (EP 08 08 824A3; Imashiro and Kuroda Tetrahedron Letters 2001 42:1313-1315). Treatment of bromoadamantane with 1 under the influence of zinc chloride (Reetz et al. Chem. Int. Ed. Engl. 1979 18:72, Reetz and Heimbach Chem. Ber. 1983 116:3702-3707, Reetz et al. Chem. Ber. 1983 116:3708-3724) yields adamantan-1-yl-dichloro-acetic acid methyl ester of Formula VII. Adamantan-1-yl-dichloro-acetic acid methyl ester of Formula VII is then hydroxylated with nitric oxide in concentrated sulfuric acid to provide a quantitative yield of dichloro-(3-hydroxy-adamantan-1-yl)-acetic acid methyl ester of Formula VIII. Hydrolysis of Formula VIII with aqueous sodium hydroxide in methanol at room temperature yields dichloro-(3-hydroxy-adamantan-1-yl)-acetic acid of Formula IX. Subsequent treatment of dichloro-(3-hydroxy-adamantan-1-yl)-acetic acid (Formula IX) with a weak base, preferably sodium bicarbonate, at elevated temperature results in the exclusive formation of the intermediate compound 3-hydroxy-<a-oxotricyclo[3.3.1.1$^{3,7}$]decane-1-acetic acid (Formula II). Also see Examples 26 through 29.

acid to lower pH to less than about 0.50 preferably about 0.20, to form the corresponding keto acid II, which may be recrystallized from water to form crystals of the keto acid II.

Another aspect of the present invention relates to a method for production of the fragment (1S,3S,5S)-2-azabicyclo[3.1.0]hexane-3-carboxamide (Formula J). This fragment used in the production of (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile can be produced in accordance with the method depicted in Scheme VI shown below.

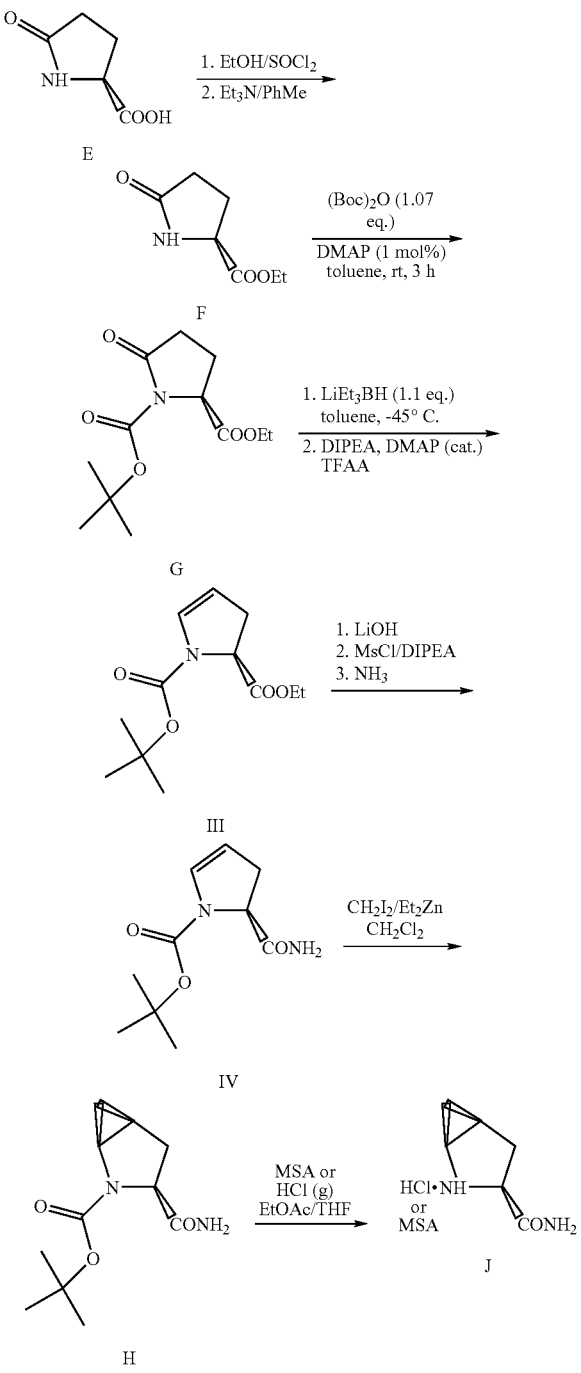

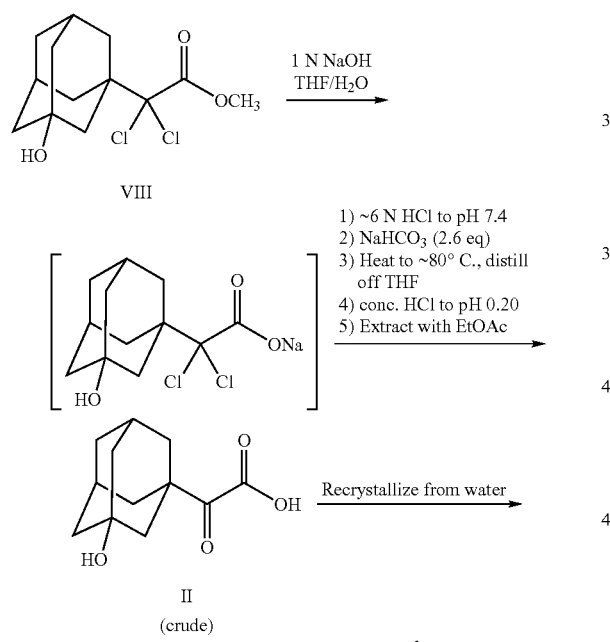

As shown in Scheme VA, the intermediate compound 3-hydroxy-a-oxotricyclo-[3.3.1.1$^{3,7}$]decane-1-acetic acid (Formula II) may be prepared in a one pot procedure. As seen, treatment of Formula VIII compound with aqueous sodium hydroxide in tetrahydrofuran (or other base such as potassium hydroxide or lithium hydroxide) in an inert atmosphere such as argon, yields the corresponding sodium salt. Without recovering the sodium salt, the reaction mixture containing the sodium salt is treated with an acid such as hydrochloric As shown in Scheme VI, L-pyroglutamic acid (Formula E) is first esterified to produce the L-pyroglutamic acid ethyl ester (Formula F; SQ 7539). This L-pyroglutamic acid ethyl ester is then BOC-protected on the nitrogen to produce (5S)-2-oxopyrrolidine-1,5-dicarboxylic acid, 1-(1,1-dimethylethyl),5-ethyl ester (Formula G). SuperHydride reduction and elimination is then performed to form 4,5-dihydro-1H-pyrrole-1,5-dicarboxylic acid, 1-(1,1-dimethylethyl),5-ethyl ester (Formula III). The BOC-DHPEE III is then hydrolyzed by saponification with lithium hydroxide to form BOC-DHP. An amide is then formed on BOC-DHP via mixed anhydride using mesyl chloride followed by ammonia to produce (5S)-5-aminocarbonyl-4,5-dihydro-1H-pyrrole-1-carboxylic acid, 1-(1,1-dimethylethyl) ester (Formula IV). (5S)-5-aminocarbonyl-4,5-dihydro-1H-pyrrole-1-carboxylic acid, 1-(1,1-dimethylethyl)ester (Formula IV) is then cyclopropanated via the Simmons-Smith reaction to produce [1S-(1<a,3<b,5<a]-3-aminocarbonyl)-2-azabicyclo[3.1.0]hexane-2-carboxylic acid, 1,1-dimethylethyl ester (Formula H). BOC is then removed resulting in formation of an acid salt such as the hydrochloride salt or the methanesulfonic acid salt of the fragment (1S,3S,5S)-2-azabicyclo[3.1.0]hexane-3-carboxamide (Formula J). Also see Examples 29 through Example 35.

Another aspect of the present invention also depicted in Scheme VI relates to the transformation of (5S)-5-aminocarbonyl-4,5-dihydro-1H-pyrrole-1-carboxylic acid, 1-(1,1-dimethylethyl) ester (Formula IV) to [1S-(<a,3<b,5<a]-3-aminocarbonyl)-2-azabicyclo[3.1.0]hexane-2-carboxylic acid, 1,1-dimethylethyl ester (Formula H) by cyclopropanation in a Simmons-Smith Reaction. In this reaction, (5S)-5-aminocarbonyl-4,5-dihydro-1H-pyrrole-1-carboxylic acid, 1-(1,1-dimethylethyl)ester is dissolved in methylene chloride in a first reactor. In a second reactor, methylene chloride is cooled to −30° C. and dimethoxy ethane and a 30% solution of diethyl zinc in toluene are added followed by addition of diiodo methane. This mixture is then added to the first reactor followed by addition of saturated bicarbonate solution. The resulting reaction mixture is stirred until a precipitate formed. The precipitate is then filtered, washed and resuspended in methylene chloride two or more times. Filtrates are then separated into aqueous and organic phases and the organic phase is washed with half saturated brine. Solvent is removed and exchanged by heptane to obtain a slurry of crude product of [1S-(1<a,3<b,5<a]-3-aminocarbonyl)-2-azabicyclo[3.1.0] hexane-2-carboxylic acid, 1,1-dimethylethyl ester (Formula H) in heptane.

Alternatively, (5S)-5-aminocarbonyl-4,5-dihydro-1H-pyrrole-1-carboxylic acid, 1-(1,1-dimethylethyl)ester (Formula IV) may be prepared as shown in Scheme VIA.

-continued

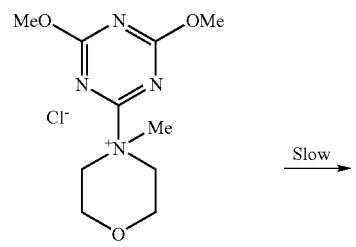

$C_{10}H_{17}ClN_4O_3$
Mol. Wt.: 276.72

4-(4,6-dimethoxy-1,3,5-triazin-2-yl)-
4-methylmorpholiniumchloride
CAS 3945-69-5 (DMT-MM)

Slow →

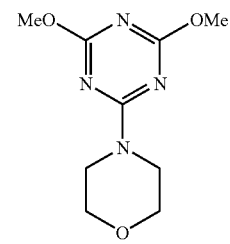

DMMT

+ MeCl

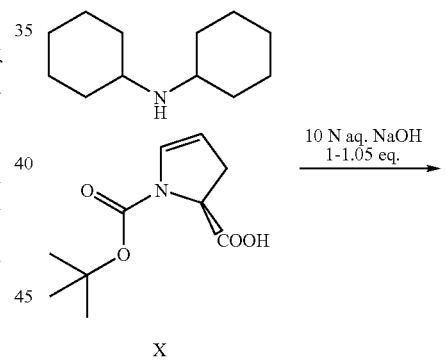

X $C_{22}H_{38}N_2O_4$
Mol. Wt.: 394.55

-BMS-587582
DCHA

10 N aq. NaOH
1-1.05 eq. →

SCHEME VIA

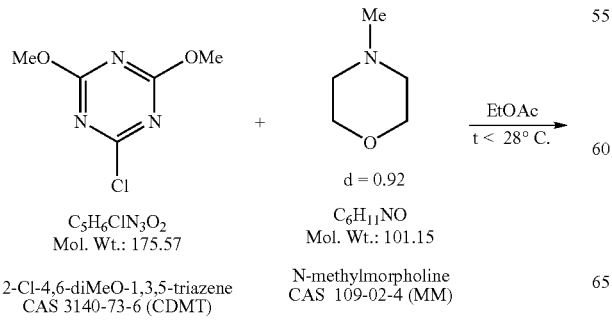

$C_5H_6ClN_3O_2$
Mol. Wt.: 175.57

2-Cl-4,6-diMeO-1,3,5-triazene
CAS 3140-73-6 (CDMT)

$C_6H_{11}NO$
Mol. Wt.: 101.15

N-methylmorpholine
CAS 109-02-4 (MM)

EtOAc
t < 28° C. → d = 0.92

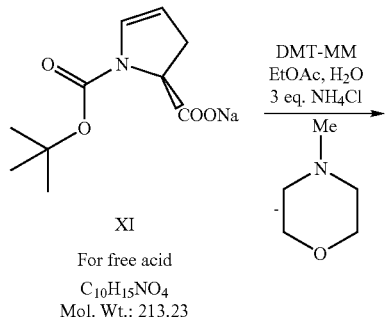

XI

For free acid $C_{10}H_{15}NO_4$
Mol. Wt.: 213.23

DMT-MM
EtOAc, H₂O
3 eq. NH₄Cl →

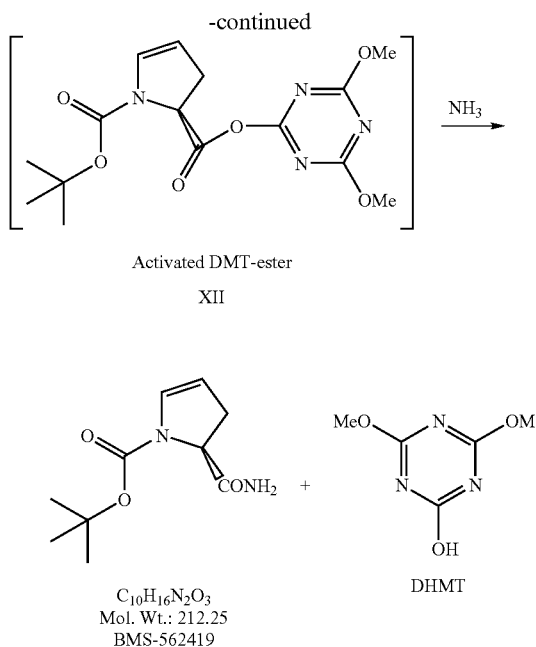

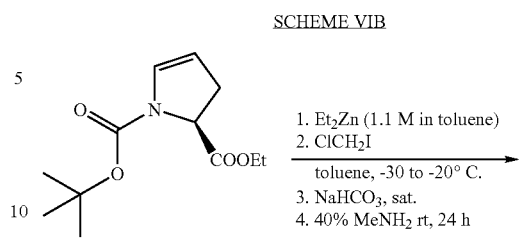

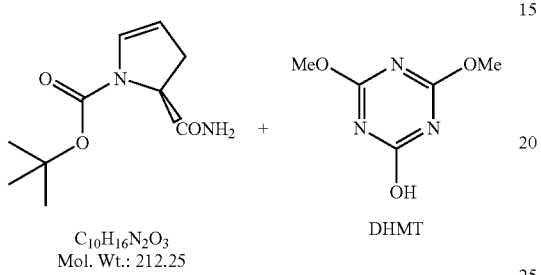

As shown in Scheme VIA, the DCHA salt of 4,5-dihydro-1H-pyrrole-1,5-dicarboxylic acid, 1-(1,1-dimethylethyl)ester X is treated with alkali metal base such as sodium hydroxide to form the corresponding salt, such as the sodium salt.

The sodium salt of 4,5-dihydro-1H-pyrrole-1,5-dicarboxylic acid, 1-(1,1-dimethylethyl)ester XI may also be prepared from the corresponding ethyl ester by treating the ethyl ester (preferably a solution of the ethyl ester in toluene) with ethanol and sodium hydroxide.

A solution of the sodium salt XI is treated with buffer such as ammonium chloride and sodium dihydrogen phosphate to lower pH of the solution below 7, preferably about 6 to 6.5, and the buffered solution of sodium salt is treated with 4-(4,6-dimethoxy-1,3,5-triazin-2-yl)-4-methylmorpholinium chloride (DMT-MM) to form the activated DMT-ester XII which is treated with ammonia or other base such as ammonium sulfate, ammonium chloride or ammonium hydroxide, to form (5S)-5-aminocarbonyl-4,5-dihydro-1H-pyrrole-1-carboxylic acid 1-(1,1-dimethylethyl)ester IV.

4-(4,6-Dimethoxy-1,3,5-triazin-2-yl)-4-methyl-morpholinium chloride (DTM-MM) may be prepared as shown in Scheme VIA by reacting 2-Cl-4,6-dimethoxy-1,3,5-triazine (CDMT) and N-methylmorpholine at reduced temperatures ranging from about 0 to about 10° C. to form DMT-MM.

The DCHA salt of 4,5-dihydro-1H-pyrrole-1,5-dicarboxylic acid, 1-(1,1-dimethylethyl)ester X may be prepared from the corresponding sodium salt XI by treating an aqueous solution of previously prepared DCHA salt X with methyl t-butyl ether (MTBE) adjusting pH of the reaction mixture to 2.5-3 employing an acid such as $H_3PO_4$. The organic layer is separated and treated with brine to form the corresponding sodium salt XI. The resulting reaction mixture is cooled and treated with DCHA to form the corresponding DCHA salt X.

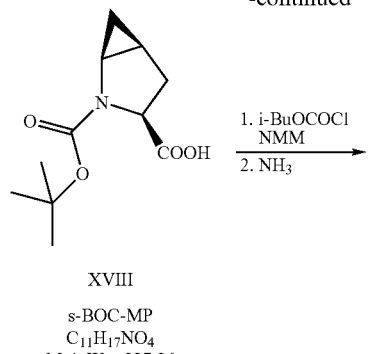

XVIII
s-BOC-MP
C₁₁H₁₇NO₄
Mol. Wt.: 227.26

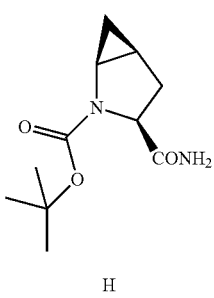

H
s-BOC-MPA
C₁₁H₁₈N₂O₃
Mol. Wt.: 226.27

Compound H Scheme VI may also be prepared as shown in Scheme VIB by cyclopropanation of N-BOC 4,5-dehydroproline ethyl ester III as follows.

N-BOC 4,5-dehydroproline ethyl ester III is treated with diethyl zinc and chloro iodomethane in the presence of dry organic solvent such as toluene, methylene chloride or dichloroethane at a reduced temperature ranging from about −30 to about 0° C. to form N-BOC 4,5-methanoproline ethyl ester XV.

The resulting BOC 4,5-methanoproline ethyl ester XV (mixture of syn- and anti-isomers (8:1)) is separated by treating with aqueous methyl amine under an inert atmosphere such as a nitrogen atmosphere and syn (S)-BOC-4,5-methaneproline ethyl ester XVI (separated from XVII) is recovered.

The s-BOC-4,5-methanoproline ethyl ester XVI in ethanol or other organic solvent such as toluene or THF is treated with base such as aqueous lithium hydroxide, sodium hydroxide or potassium hydroxide to form the corresponding s-BOC-methanoproline free acid XVIII.

The free acid XVIII is converted to the corresponding s-BOC-methanoproline amide H by treating free acid XVIII dissolved in an organic solvent such as THF or methylene chloride; isobutyl chloroformate or mesyl chloride, in the presence of N-methyl morpholine, under reduced temperatures such as not to exceed about −8° C., and then treating the reaction mixture with ammonia to form the s-BOC-methanoproline amide H.

Another aspect of the present invention relates to a method for coupling the fragments (<aS)-<a-amino-3-hydroxytricyclo[3.3.1.1³,⁷]decane-1-acetic acid (Formula V) and (1S,3S, 5S)-2-azabicyclo[3.1.0]hexane-3-carboxamide (Formula J) to produce (1S,3S,5S)-2-[(2S)-2-amino-2-(3-hydroxytricyclo[3.3.1.1³,⁷]dec-1-yl)-1-oxoethyl]-2-azabicyclo[3.1.0] hexane-3-carbonitrile, benzoate (1:1). Coupling of these fragments is depicted in Scheme VII below.

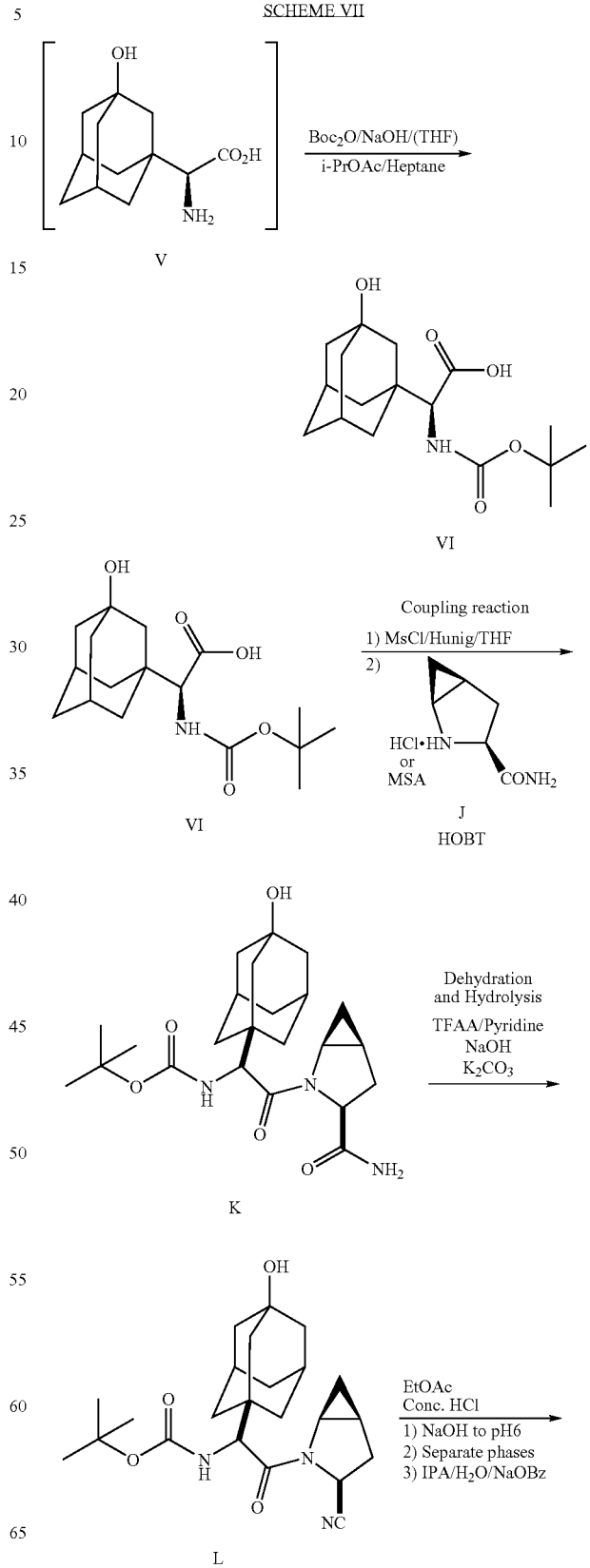

-continued

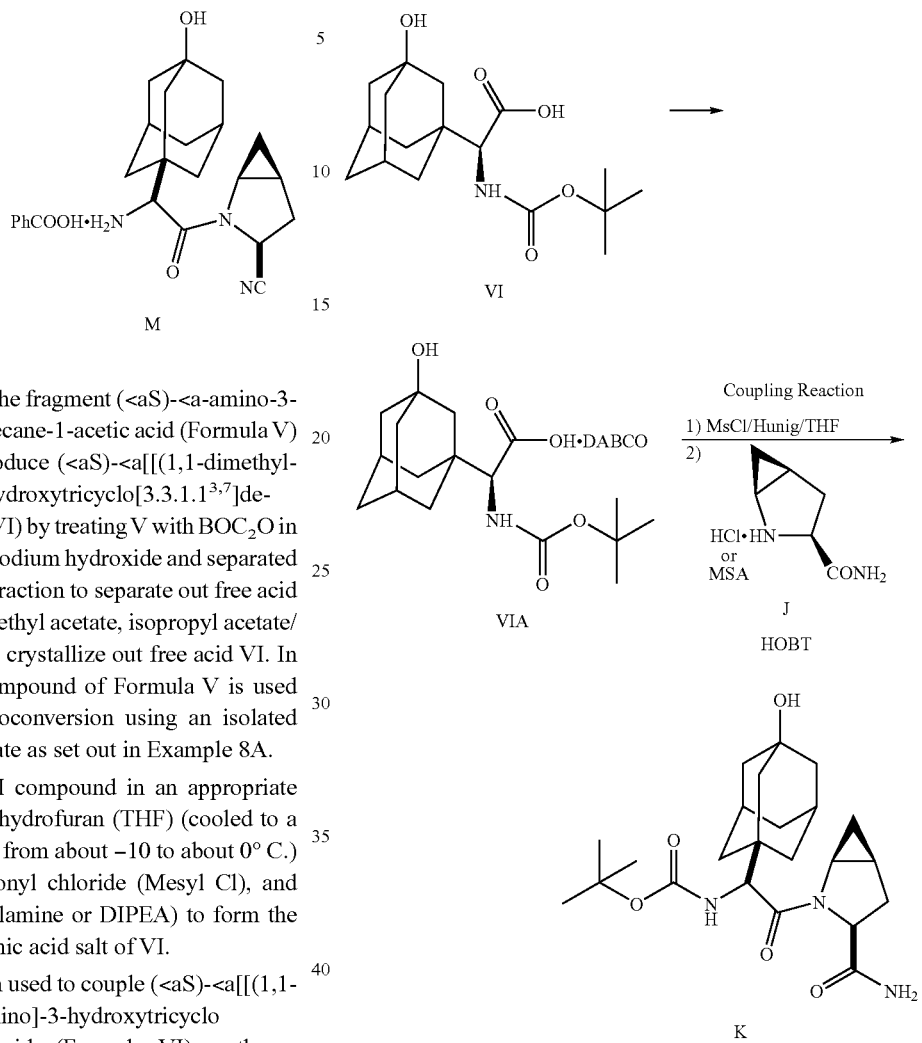

SCHEME VIIA

As shown in Scheme VII, the fragment (<aS)-<a-amino-3-hydroxytricyclo[3.3.1.1³,⁷]decane-1-acetic acid (Formula V) is first BOC protected to produce (<aS)-<a[[(1,1-dimethylethoxy)carbonyl]amino]-3-hydroxytricyclo[3.3.1.1³,⁷]decane-1-acetic acid (Formula VI) by treating V with BOC₂O in the presence of base such as sodium hydroxide and separated via ethyl acetate (EtOAc) extraction to separate out free acid VI. Alternatively, in place of ethyl acetate, isopropyl acetate/heptane may be employed to crystallize out free acid VI. In another embodiment, the compound of Formula V is used without isolation from a bioconversion using an isolated PDH/FDH enzyme concentrate as set out in Example 8A.

A solution of Formula VI compound in an appropriate organic solvent such as tetrahydrofuran (THF) (cooled to a temperature within the range from about −10 to about 0° C.) is treated with methanesulfonyl chloride (Mesyl Cl), and Hunig base (diisopropylethylamine or DIPEA) to form the corresponding methanesulfonic acid salt of VI.

A coupling reaction is then used to couple (<aS)-<a[[(1,1-dimethylethoxy)carbonyl]amino]-3-hydroxytricyclo[3.3.1.1³,⁷]decane-1-acetic acid, (Formula VI) methanesulfonic acid salt to (1S,3S,5S)-2-azabicyclo[3.1.0]hexane-3-carboxamide (Formula J) in the presence of 1-hydroxybenzotriazole (HOBT) or other known coupling agent to produce 3-(aminocarbonyl)-<aS)-<a-(3-hydroxytricyclo[3.3.1.1³,⁷]dec-1-yl)-<b-oxo-(1S,3S,5S)-2-azabicyclo[3.1.0]hexane-2-ethanecarbamic acid, 1,1-dimethylethyl ester (Formula K). Formula K compound is subjected to dehydration by treating compound K with organic base such as pyridine or triethylamine and trifluoroacetic anhydride, and then subjecting the reaction to hydrolysis by cooling to from about 0 to about 10° C. and adding sodium hydroxide or other strong base such as KOH or LiOH to form Compound L. 3-cyano-(<aS)-<a-(3-hydroxytricyclo[3.3.1.1 ³,⁷]dec-1-yl)-<b-oxo-(1S,3S,5S)-2-azabicyclo[3.1.0]hexane-2-ethanecarbamic acid, 1,1-dimethylethyl ester (Formula L), which is then deprotected (and treated with sodium benzoate) to form the dipeptidyl peptidase IV inhibitor (1S,3S,5S)-2-[(2S)-2-amino-2-(3-hydroxytricyclo[3.3.1.1 ³,⁷]dec-1-yl)-1-oxoethyl]-2-azabicyclo[3.1.0]hexane-3-carbonitrile, benzoate (1:1) (Formula M). Also see Examples 37 through 39 herein.

As shown in Scheme VIIA, compound K may also be prepared from the compound VIA (DABCO salt) as follows.

Formula VI acid is treated with 1,4-diazabicyclo[2,2,2]octane (DABCO) to form (<aS)-<a[[(1,1-dimethylethoxy)carbonyl]amino]-3-hydroxytricyclo[3.3.1.1³,⁷]decane-1-acetic acid, 1,4-diazabicyclo[2.2.2]octane salt (Formula VIA). A coupling reaction (as described in Scheme VIIA) is then used to couple (<aS)-<a[[(1,1-dimethylethoxy)carbonyl]amino]-3-hydroxytricyclo[3.3.1.1³,⁷]decane-1-acetic acid, 1,4-diazabicyclo[2.2.2]octane salt (Formula VIA) to (1S,3S,5S)-2-azabicyclo[3.1.0]hexane-3-carboxamide HCl or MSA salt (Formula J) in the presence of 1-hydroxybenzotriazole (HOBT) or other known coupling agent to produce 3-(aminocarbonyl)-<aS)-<a-(3-hydroxytricyclo[3.3.1.1³,⁷]dec-1-yl)-<b-oxo-(1S,3S,5S)-2-azabicyclo[3.1.0]hexane-ethanecarbamic acid, 1,1-dimethylethyl ester (Formula K).

Referring back to Scheme VII, compound L may be deprotected by treatment with strong acid such as hydrochloric acid as described with respect to Scheme VIIB.

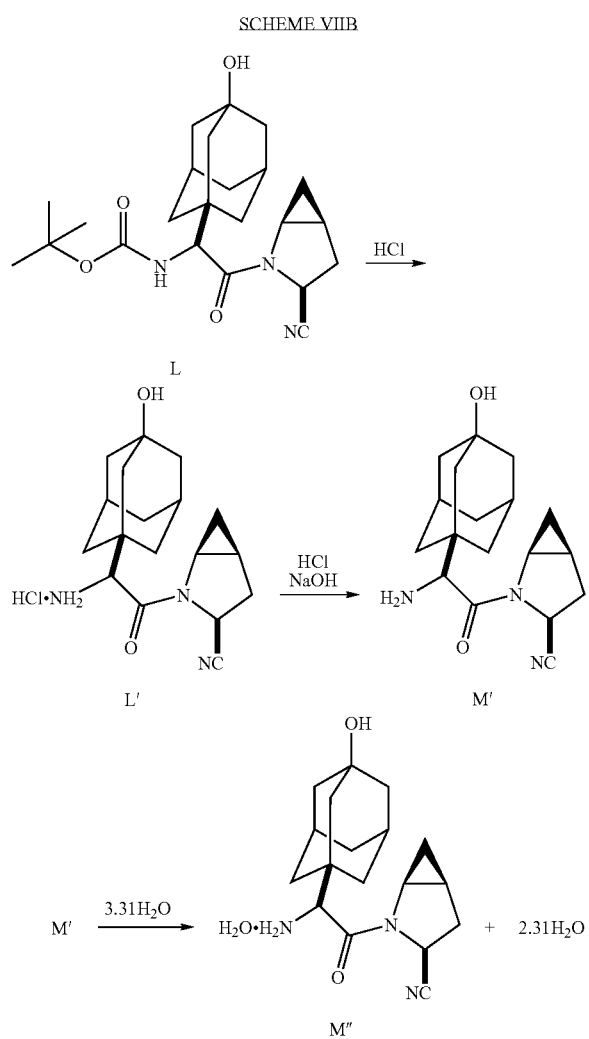

SCHEME VIIB

Referring to Scheme VIIB, the free base monohydrate M" may be formed from the BOC-protected intermediate L as follows.

BOC-protected intermediate L is treated with concentrated hydrochloric acid in the presence of methylene chloride and methanol while maintaining reaction temperature within the range from about 20 and 25° C., to form hydrochloride salt L'. Hydrochloride salt L' is treated with sodium hydroxide or other strong base to form the free base M'. Free base M' is then treated with water to form the free base monohydrate M".

As will be understood by those of skill in the art upon reading this disclosure, the final product, the dipeptidyl peptidase IV inhibitor (1S,3S,5S)-2-[(2S)-2-amino-2-(3-hydroxytricyclo[3.3.1.1$^{3,7}$]dec-1-yl)-1-oxoethyl]-2-azabicyclo [3.1.0]hexane-3-carbonitrile, benzoate (1:1) (Formula M) or its corresponding free base M' or monohydrate M" thereof can be produced using all the steps depicted in Schemes I, II, or III and IV, V, VI, VII and VIIA or only a portion of the steps depicted in any of Schemes I, II, or III and IV, V, VI, VII and VIIA depending upon which intermediate is selected as the starting material. For example, using the teachings of the present invention, one of skill in the art can routinely produce the cyclopropyl-fused pyrrolidine-based inhibitor (1S,3S, 5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) (Formula M) or the corresponding free base M' using 3-hydroxy-<a-oxotricyclo[3.3.1.1$^{3,7}$]decane-1-acetic acid of Formula II, (<aS)-<a-amino-3-hydroxytricyclo [3.3.1.1$^{3,7}$]decane-1-acetic acid of Formula V, (<aS)-<a[[(1, 1-dimethylethoxy)carbonyl]amino]-3-hydroxytricyclo [3.3.1.1$^{3,7}$]decane-1-acetic acid, 1,4-diazabicyclo[2.2.2] octane salt of Formula VIA, or (5S)-5-aminocarbonyl-4,5-dihydro-1H-pyrrole-1-carboxylic acid, 1-(1,1-dimethylethyl)ester of Formula IV as the starting material.

Thus, one of skill in the art can produce a cyclopropyl-fused pyrrolidine-based inhibitor of dipeptidyl peptidase IV simply by coupling (<aS)-<a[[(1,1-dimethylethoxy)carbonyl]amino]-3-hydroxytricyclo[3.3.1.1$^{3,7}$]decane-1-acetic acid, (Formula VI) (or its DABCO salt (Formula VIA)) to (1S,3S,5S)-2-azabicyclo[3.1.0]hexane-3-carboxamide (Formula J) to produce 3-(aminocarbonyl)-<aS)-<a-(3-hydroxytricyclo[3.3.1.1$^{3,7}$]dec-1-yl)-<b-oxo-(1S,3S,5S)-2-azabicyclo[3.1.0]hexane-2-ethanecarbamic acid, 1,1-dimethylethyl ester (Formula K); dehydrating 3-(aminocarbonyl)-<aS)-<a-(3-hydroxytricyclo[3.3.1.1$^{3,7}$] dec-1-yl)-<b-oxo-(1S,3S,5S)-2-azabicyclo[3.1.0]hexane-2-ethanecarbamic acid, 1,1-dimethylethyl ester (Formula K) to produce 3-cyano-(<aS)-<a-(3-hydroxytricyclo[3.3.1.1$^{3,7}$] dec-1-yl)-<b-oxo-(1S,3S,5S)-2-azabicyclo[3.1.0]hexane-2-ethanecarbamic acid, 1,1-dimethylethyl ester (Formula L); and hydrolyzing 3-cyano-(<aS)-<a-(3-hydroxytricyclo [3.3.1.1$^{3,7}$]dec-1-yl)-<b-oxo-(1S,3S,5S)-2-azabicyclo [3.1.0]hexane-2-ethanecarbamic acid, 1,1-dimethylethyl ester (Formula L) to form the dipeptidyl peptidase IV inhibitor. In this method, the starting materials comprise the fragments, (<aS)-<a[[(1,1-dimethylethoxy)carbonyl]amino]-3-hydroxytricyclo[3.3.1.1$^{3,7}$]decane-1-acetic acid, (Formula VI) (or its DABCO salt (Formula VIA)) and (1S,3S,5S)-2-azabicyclo[3.1.0]hexane-3-carboxamide (Formula J).

However, the method may further comprise steps for production of the fragment (<aS)-<a[[(1,1-dimethylethoxy)carbonyl]amino]-3-hydroxytricyclo[3.3.1.1$^{3,7}$]decane-1-acetic acid (Formula VI) from the intermediate (<aS)-<a-amino-3-hydroxytricyclo[3.3.1.1$^{3,7}$]decane-1-acetic acid (Formula V) via BOC protection. In this embodiment, the method may further comprise production of the (<aS)-<a-amino-3-hydroxytricyclo[3.3.1.1$^{3,7}$]decane-1-acetic acid (Formula V) intermediate by asymmetrically reducing 3-hydroxy-<a-ox-otricyclo[3.3.1.1$^{3,7}$]decane-1-acetic acid (Formula II) by enzymatic amination or transamination (see Scheme I or II). Alternatively, the method may further comprise chemical synthesis of (<aS-<a-amino-3-hydroxytricyclo[3.3.1.1$^{3,7}$] decane-1-acetic acid (Formula V) from tricyclo[3.3.1.1$^{3,7}$] decane-1-acetic acid (Formula N) in accordance with Scheme III.

In addition, or alternatively, the method may further comprise steps for production of the fragment (1S,3S,5S)-2-azabicyclo[3.1.0]hexane-3-carboxamide (Formula J) by removal of BOC from the intermediate [1S-(1<a,3<b,5<a]-3-aminocarbonyl)-2-azabicyclo[3.1.0]hexane-2-carboxylic acid, 1,1-dimethylethyl ester (Formula H). In this embodiment, the method may further comprise a step for production of [1S-(1<a,3<b,5<a]-3-aminocarbonyl)-2-azabicyclo[3.1.0] hexane-2carboxylic acid, 1,1-dimethylethyl ester (Formula H) by cyclopropanation, preferably via a Simmons-Smith reaction of (5S)-5-aminocarbonyl-4,5-dihydro-1H-pyrrole-1-carboxylic acid, 1-(1,1-dimethylethyl) ester (Formula IV).

Another aspect of the present invention relates to new compounds identified herein as being useful intermediates in the production of cyclopropyl-fused pyrrolidine-based inhibitors of dipeptidyl peptidase IV. Compounds of the present invention useful as intermediates in the production of cyclopropyl-fused pyrrolidine-based inhibitors of dipeptidyl peptidase IV include:

3-hydroxy-α-oxotricyclo[3.3.1.1³,⁷]decane-1-acetic acid, methyl ester as depicted in Formula I,

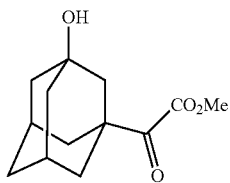

I 3-hydroxy-α-oxotricyclo[3.3.1.1³,⁷]decane-1-acetic acid as depicted in Formula II,

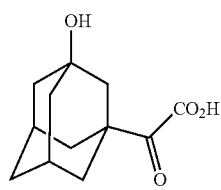

II (5S)-5-aminocarbonyl-4,5-dihydro-1H-pyrrole-1-carboxylic acid, 1-(1,1-dimethylethyl)ester as depicted in Formula IV,

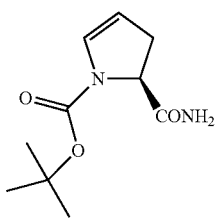

IV (αS)-α-amino-3-hydroxytricyclo[3.3.1.1³,⁷]decane-1-acetic acid as depicted in Formula V,

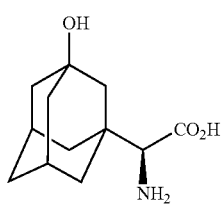

V (αS)-α[[(1,1-dimethylethoxy)carbonyl]amino]-3-hydroxytricyclo[3.3.1.1³,⁷]decane-1-acetic acid as depicted in Formula VI,

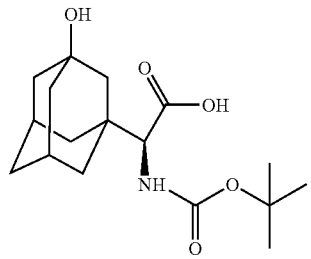

VI (or its DABCO salt VIA), adamantan-1-yl-dichloro-acetic acid methyl ester as depicted in Formula VII,

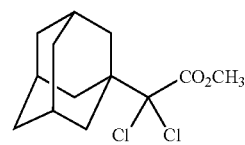

VII dichloro-(3-hydroxy-adamantan-1-yl)-acetic acid methyl ester as depicted in Formula VIII, and

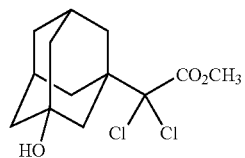

VIII dichloro-(3-hydroxy-adamantan-1-yl)-acetic acid as depicted in Formula IX.

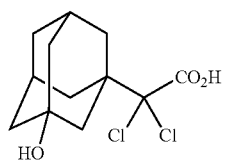

IX

In a preferred embodiment, as shown herein, these compounds are used as intermediates in the production of the dipeptidyl peptidase IV inhibitors (1S,3S,5S)-2-[(2S)-2-amino-2-(3-hydroxytricyclo[3.3.1.1³,⁷]dec-1-yl)-1-oxoethyl]-2-azabicyclo[3.1.0]hexane-3-carbonitrile, benzoate (1:1) as depicted in Formula M.

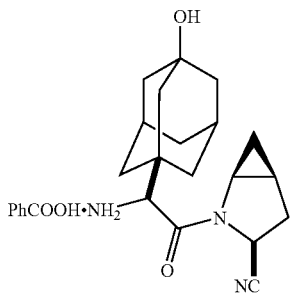

and preferably the corresponding free base or its monohydrate as depicted in Formulas M' and M", respectively

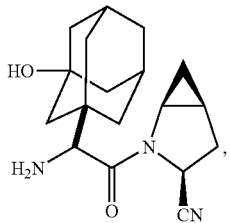

or its monohydrate M" (set out hereinbefore).

Dipeptidyl peptidase IV inhibition produced using the compounds and methods of the present invention are useful in the treatment of diabetes and complications thereof, hyperglycemia, Syndrome X, hyperinsulinemia, obesity, and atherosclerosis and related diseases as well as immunomodulatory diseases and chronic inflammatory bowel disease.

The following Examples represent preferred embodiments of the invention.

EXAMPLES

Example 1

Reductive Amination using an Extract from Recombinant *Pichia pastoris* Expressing Phenylalanine Dehydrogenase from *Thermoactinomyces intermedius* and Producing an Endogenous Formate Dehydrogenase Recombinant *Pichia pastoris* frozen cells (2.25 kg) expressing phenylalanine dehydrogenase from *Thermoactinomyces intermedius* were added to deionized water (6.75 L) containing ammonium formate (28.65 g, 0.454 moles). After thawing, the cells were suspended using a Janke and Kunkel Ultra-turrax T25 homogenizer, adjusted to pH 7 with concentrated NH$_4$OH and cooled with crushed ice to give a 25% w/v cell suspension in 50 mM ammonium formate. Cells were disrupted by 2 passages through a microfluidizer at 12000 psi and cell debris was removed by centrifugation at 20,000×g and 4° C. Supernatant, 7024 ml containing 230998 units or 124641 units of phenylalanine dehydrogenase activity as determined by Assay A (see Example 9) or Assay B (see Example 10), respectively, and 80080 units formate dehydrogenase were added to a 16 L vessel of a New Brunswick Scientific Bioflo IV bioreactor.

A 7024 ml solution was prepared containing ammonium formate (442.5 grams, 7.017 moles) and (3-hydroxy-adamantan-1-yl)-oxo-acetic acid (786.7 grams, 3.510 moles). The pH of this solution was adjusted to 8.0 with 276 ml concentrated ammonium hydroxide. Nicotinamide adenine dinucleotide (AND; 9.834 grams, 14.82 mmoles) and dithiothreitol (2.163 grams, 14.027 mmoles) were then added and the solution was added to the bioreactor containing the *Pichia pastoris* extract. The solution was maintained at 40° C. and stirred at 150 rpm. Aliquots of concentrated ammonium hydroxide of 45, 25 and 27 ml were added at 0, 3 and 18 hours, respectively, after the start of the reaction to adjust the pH to 8.0. After 25 hours, the solution contained 818.9 grams (3.637 moles, 100% yield) (S)-amino-(3-hydroxy-adamantan-1-yl)-acetic acid as measured by HPLC analysis (see Example 8, Method 2) and no detectable keto acid or R-enantiomer of the amino acid.

(S)-amino-(3-hydroxy-adamantan-1-yl)-acetic acid was isolated via a procedure consisting of boiling the enzymatic transformation mixture to drive off ammonia, adjusting to pH 3 with formic acid, filtration to remove precipitated proteins, sorption of the amino acid on Dowex 50 (H+) resin, elution with 1.5 M ammonia and concentration of the rich effluent to give (<aS)-<a-amino-3-hydroxytricyclo[3.3.1.1$^{3,7}$]decane-1-acetic acid as a crystalline solid. The last run using this isolation procedure (787 grams ketoacid input) gave 804 grams of (<aS)-<a-amino-3-hydroxytricyclo[3.3.1.1$^{3,7}$]decane-1-acetic acid with a potency of 94.3% and a yield of 96.0% from 3-hydroxy-<a-oxotricyclo[3.3.1.1$^{3,7}$]decane-1-acetic acid. All of the batches of (<aS)-<a-amino-3-hydroxytricyclo[3.3.1.1$^{3,7}$]decane-1-acetic acid isolated by this procedure performed well in subsequent reactions en route to (1S,3S,5S)-2-[(2S)-2-amino-2-(3-hydroxytricyclo[3.3.1.1$^{3,7}$]dec-1-yl)-azabicyclo[3.1.0]hexane-3-carbonitrile, benzoate.

Example 2

Reductive Amination using Heat-Dried Cells from Recombinant *Pichia pastoris*

A solution was prepared containing in a final volume of 4.0 ml at pH 8.0 (pH adjusted with NH$_4$OH): 0.50 M ammonium formate, 0.25 M (3-hydroxy-adamantan-1-yl)-oxo-acetic acid, 1.06 mM AND, 1.00 mM dithiothreitol, and 250 mg recombinant *Pichia pastoris* heat-dried cells containing 32.7 units, as determined by Assay A, phenylalanine dehydrogenase and 24.6 units formate dehydrogenase. Preparation of *Pichia pastoris* heat-dried cells has been described by Hanson et al. (Enzyme and Microbial Technology 2000 26:348-358). The solution was incubated in a 50 ml Erlenmeyer flask at 40° C., 100 rpm for 4 days, then analyzed by HPLC. The solution contained 45.02 mg/ml (80% yield) (S)-amino-(3-hydroxy-adamantan-1-yl)-acetic acid.

Example 3

Reductive Amination using Wet Cells from Recombinant *Pichia pastoris*

A solution was prepared containing in a final volume of 3.0 ml at pH 8.0 (pH adjusted with NH$_4$OH): 0.415 M ammonium formate, 0.208 M (3-hydroxy-adamantan-1-yl)-oxo-acetic acid, 0.88 mM AND, 0.84 mM dithiothreitol, and 12.5% % w/v *Pichia pastoris* wet cells containing 6.06 units phenylalanine dehydrogenase, as determined by Assay A, and 12.8 units formate dehydrogenase. The solution was incubated in a 50 ml Erlenmeyer flask at 40° C., 200 rpm for 68 hours, then analyzed by HPLC. The solution contained 31.9 mg/ml (68% yield) (S)-amino-(3-hydroxy-adamantant-1-yl)-acetic acid.

Example 4

Reductive Amination using Recombinant *Escherichia coli* Heat-Dried Cells Expressing Phenylalanine Dehydrogenase from *Thermoactinomyces intermedius* and Formate Dehydrogenase from *Candida boidinii*

A solution was prepared containing in a final volume of 4.0 ml at pH 8.0 (pH adjusted with $NH_4OH$): 0.50 M ammonium formate, 0.25 M (3-hydroxy-adamantan-1-yl)-oxo-acetic acid, 1.06 mM AND, 1.00 mM dithiothreitol, 2.55 units/ml (0.51 units/mg) formate dehydrogenase from *Candida boidinii* (Boehringer Mannheim), and 250 mg recombinant *Escherichia coli* heat-dried cells containing 76 units, as determined by Assay A, phenylalanine dehydrogenase. The solution was incubated in a 50 ml Erlenmeyer flask at 40° C., 100 rpm for 4 days, then analyzed by HPLC. The solution contained 7.69 mg/ml (13.7% yield) (S)-amino-(3-hydroxy-adamantan-1-yl)-acetic acid.

Example 5

Reductive Amination using Recombinant *Escherichia coli* Wet Cells and Formate Dehydrogenase from *Candida boidinii*

A solution was prepared containing in a final volume of 3.0 ml at pH 8.0 (pH adjusted with $NH_4OH$): 0.415 M ammonium formate, 0.208 M (3-hydroxy-adamantan-1-yl)-oxo-acetic acid, 0.88 mM AND, 0.84 mM dithiothreitol, 1 unit/ml (0.51 units/mg) formate dehydrogenase from *Candida boidinii* (Boehringer Mannheim), and 12.5% w/v *Escherichia coli* wet cell containing 97 units, as determined by Assay A, phenylalanine dehydrogenase. The solution was incubated in a 50 ml Erlenmeyer flask at 40° C., 200 rpm for 68 hours, then analyzed by HPLC. The solution contained 5.16 mg/ml (11.0% yield) (S)-amino-(3-hydroxy-adamantant-1-yl)-acetic acid.

Example 6

Reductive Amination using Phenylalanine Dehydrogenase from *Sporosarcina* species and Formate Dehydrogenase from *Candida boidinii*

A solution was prepared containing in a final volume of 1.0 ml at pH 8.5 (pH adjusted with $NH_4OH$: 0.15 M ammonium formate, 0.05M (11.2 mg/ml) (3-hydroxy-adamantan-1-yl)-oxo-acetic acid, 1 mM AND, 1 mM dithiothreitol, 0.51 units/ml (0.51 units/mg) formate dehydrogenase from *Candida boidinii* (Boehringer Mannheim) and 1.01 units/ml phenylalanine dehydrogenase (14.5 units/mg; Sigma Chemical Co.) from *Sporosarcina* species. The solution was incubated at 30° C. for 20 hours, then analyzed by HPLC. The solution contained 0.31 mg/ml (2.74% yield) (S)-amino-(3-hydroxy-adamantant-1-yl)-acetic acid.

Example 7

Construction of Plasmid pBMS2000-PPFDH-PDHmod

A two-step construction of the expression vector pBMS2000-PPFDH-PDHmod was employed. The *P. pastoris* FDH gene was subcloned into expression vector pBMS2000 (pBMS2000 is disclosed in U.S. Pat. No. 6,068,991, issued May 30, 2000 to S. W. Liu et al.) using oligonucleotide primers containing the 5' and 3' end of the *P. pastoris* FDH gene along with compatible restriction endonuclease cleavage sites:

```
5' TCGTCATGAAAATCGTTCTCGTTTTG 3'   (5' end; sense;
    BspHI                           SEQ ID NO:1)

5' TACTGTTTTTCCAGCGTATTCCTAGGCT 3' (3' end; anti-
                                    sense;
              BamHI                 SEQ ID NO:2)
```

High-fidelity PCR amplification of the *P. pastoris* FDH gene was carried out in four 100 µl aliquots, each containing 1 X TaqPlus reaction buffer (Stratagene, LaJolla, Calif.), 0.2 mM each deoxynucleotide triphosphate (dATP, dCTP, dGTP, and dTTP), 0.4 nM each oligonucleotide, 2.5 U TaqPlus DNA polymerase (Stratagene), and 10 pg plasmid DNA containing the cloned *P. pastoris* FDH gene. The amplification conditions included incubation at 94° C. for 4 minutes, followed by 25 cycles of incubation at 94° C. for 1 minute; 50° C. for 1 minute; and 72° C. for 1.5 minutes, using a Perkin-Elmer Model 480 thermocycler with autoextension.

The PCR reaction mixture was extracted with an equal volume of 1:1 phenol:chloroform (GibcoBRL, Gaithersburg, Md.), and centrifuged at 13,000×g for 5 minutes. The upper aqueous phase was removed and placed in a new microcentrifuge tube. DNA was precipitated by addition of 0.1 volumes 3 M sodium acetate and 2 volumes ice-cold ethanol. After centrifugation at 13,000×g for 5 minutes, liquid was aspirated from the tube, and the pellet washed with 0.5 ml ice-cold 70% ethanol. Liquid was aspirated again, and the pellet was allowed to air dry for 30 minutes at room temperature.

Amplified DNA was digested with 20 units each of BspHI and BamHI for 3 hours at 37° C. in a total volume of 50 µl. In parallel, the pBMS2000 vector (2 µg) was digested with BspHI and BamHI. The digested samples were electrophoresed on a 1.0% TAE agarose gel for 2 hours at 100 v. The bands corresponding to the FDH gene (1100-base pair fragment) and linearized vector (4700-base pair fragment) which were separately excised from the gel and purified using the QIAquick Gel Extraction Kit (Qiagen, Chatsworth, Calif.). The concentrations of the isolated fragments were estimated by electrophoresis against the low molecular weight mass ladder (Invitrogen Corp., Carlsbad, Calif.) and ligated in a 5:1 (insert:vector) molar ratio in a total volume of 10 µl at 22° C. for 2 hours. DNA was precipitated by addition of 15 µl $dH_2O$ and 250 µl 1-butanol, and pelleted at 13,000×g in a microcentrifuge for 5 minutes. Liquid was removed by aspiration, and the DNA was dried in a SpeedVac (Savant Instruments, Farmingdale, N.Y.) for 5 minutes under low heat. The pellet was resuspended in 5 µl $dH_2O$.

The resuspended DNA was transformed by electroporation into 0.04 ml *E. coli* DH10B competent cells (Invitrogen) at 25 µF and 250 Ω. SOC medium was immediately added (0.96 ml; SOC=0.5% yeast extract, 2% tryptone, 10 mM NaCl, 2.5 mM KCl, 10 mM $MgCl_2$, 10 mM $MgSO_4$, and 20 mM glucose per liter), and the cells incubated in a shaker for 1 hour at 37° C. and 225 rpm. Colonies contain plasmid DNA were selected on LB agar plates containing 50 µg/ml kanamycin sulfate (Sigma Chemicals, St. Louis, Mo.). Plasmids with the desired insert were identified by colony PCR in capillary tubes using the RapidCycler (Idaho Technology, Salt Lake City, Utah). Each reaction mixture contained 50 mM Tris-HCl (pH 8.3), 4 mM MgCl$_2$, 0.25 mg/ml bovine serum albumin, 2% sucrose 400, 0.1 mM cresol red, 0.4 nM each primer (SEQ ID NO:1 and SEQ ID NO:2), and 2.5 U Taq DNA polymerase (Promega Corp., Madison, Wis.). The reaction mixture was divided into 10 µl aliquots, and pipetted into the wells of a round-bottom microtiter plate. A kanamycin-resistant colony was picked using a disposable plastic inoculation needle, swirled into the reaction mixture, and transferred to LB-kanamycin agar. Each reaction mixture aliquot was drawn into a 30 µl capillary tube, and the tube was flame-sealed at both ends. Cells were lysed and DNA denatured by incubation at 94° C. for 30 seconds; amplification was performed using 30 cycles of incubation at 94° C. for 0 seconds; 40° C. for 0 seconds, and 72° C. for 60 seconds using a RapidCycler Thermocycler (Idaho Technologies, Salt Lake City, Utah). Samples were electrophoresed on a 1.0% TAE agarose gel for 2 hours at 100 v. Seven samples out of 17 tested showed a strong band at 1100 base pairs. One colony containing this plasmid (referred to herein as pBMS2000-PPFDH) was chosen for the next step in the plasmid construction.

"PDHmod" refers to a modified *Thermoactinomycetes intermedius* phenylalanine dehydrogenase that differs from the published DNA sequence (Takada et al., J. Biochem. 109, pp. 371-376 [1991]) by a change of the last two amino acids and an additional 12 amino acids at the carboxyl terminus that is required for complete conversion of (3-hydroxy-adamantan-1-yl)-oxo-acetic acid to (S)-amino-(3-hydroxy-adamantan-1-yl)-acetic acid. This change was introduced into plasmid pPDH9K/10 (described in detail by in patent WO 200004179, issued to Donovan et al., Jan. 27, 2000), which was subsequently transformed into *P. pastoris* SMD1168 (deposited as strain ATCC 74408).

3' end of native PDH gene and corresponding amino acids:

```
AAC AGC GCA AGG AGG TAA      (SEQ ID NO: 5)

Asn Ser Ala Arg Arg Stop     (SEQ ID NO: 6)
```

3' end of PDHmod gene and corresponding amino acids (changed or new ammo acids in bold):

```
AAC AGC GCG GAG GGG TAC CTC GAG CCG  (SEQ ID NO: 7)

Asn Ser Ala Glu Gly Tyr Leu Glu Pro  (SEQ ID NO: 8)

CGG CGG CCG CGA ATT AAT TCG CCT TAG

Arg Arg Pro Arg Ile Asn Ser Pro Stop
```

Oligonucleotide primers containing the 5' and 3' end of the PDHmod gene along with compatable restriction endonuclease cleavage sites were prepared:

```
GATGCTCATATGCGCGACGTGTTTGAAATGATG   (5' end, sense;
      NdeI                           SEQ ID NO:3)

GATCCCGGGCTAAGGCGAATTAATAATTCG      (3' end, anti-
                                    sense;
      SMaI                          SEQ ID NO:4)
```

Reaction conditions for amplification and purification of the PDHmod by PCR were identical to that used for the *P. pastoris* FDH gene except chromosomal DNA prepared from ATCC 74408 was included as template for the reaction. The resulting fragment was digested with 20 units each of NdeI and SmaI for 1 hour at 25° C., followed by 2 hours at 37° C., in a total volume of 50 µl. In parallel, a version of the pBMS2000 vector with an NdeI site at the initiation codon (2 µg) was digested with NdeI and SmaI using identical conditions. The digested samples were separately electrophoresed on a 1.0% TAE agarose gel for 2 hours at 100 v. The bands corresponding to the PDHmod gene (1200-base pair fragment) and linearized vector (4700-base pair fragment) were excised from the gel and purified using the QIAquick Gel Extraction Kit (Qiagen). Ligation of the two fragments, transformation of *E. coli*, and screening for colonies containing inserts with the PDHmod gene (forming pBMS2000-PDHmod) were performed as described supra.

For construction of pBMS2000-PPFDH-PDHmod, pBMS2000-PDHmod (2 µg) was cleaved with 10 U each HindIII and SmaI in a 50 µL reaction for 1 hour at 25° C., followed by 1 hour at 37° C. Ten units of T4 DNA polymerase (Invitrogen) and 2 µL of a 2.5 mM mixture of all four deoxyribonucleoside triphosphates were added and the sample incubated at 11° C. for 20 minutes. The reaction was electrophoresed on a 1.0% TAE agarose gel for 2 hours at 100 v. The 1800-base pair fragment was excised and isolated using the QIAquick Gel Extraction Kit (Qiagen). This fragment contains, in order, the tac promoter, groES gene, and the PDHmod gene (as a transcriptional fusion). Next, pBMS2000-PPFDH (2 µg) was digested with 10 units restriction endonuclease SmaI in a 50 µL volume for 2 hours at 25° C., then treated with 0.4 U shrimp alkaline phosphatase (United States Biochemicals, Cleveland, Ohio) for 1 hour at 37° C. Plasmid DNA was electrophoresed for 2 hours at 100 v on a 1.0% TAE agarose gel, isolated, and extracted with the QIAquick kit. The two fragments were ligated in a 6.5:1 (insert:vector) molar ratio at 16° C. for 4 hours in a 10 µL final volume. After 1-butanol extraction and centrifugation, the DNA was transformed into electrocompetent DH10B cells. Kanamycin-resistant colonies were screened for the presence of the PDHmod gene with the two PDHmod-specific primers as previously described for FDH. A second round of PCR screening was conducted by using DNA primers homologous to the 5' end of the PPFDH and 3' end of the PDHmod gene, respectively. Only those constructs able to support amplification of a 1400-base pair fragment possessed the two genes in the same orientation. One such plasmid was found and the orientation confirmed by diagnostic restriction digestion with KpnI, which gave the expected fragments of 5422 and 1826 base pairs. This plasmid was designated "pBMS2000-PPFDH-PDHmod."

Example 8

Expression of FDH and PDHmod pBMS2000-PPFDH-PDHmod was transformed into *Escherichia coli* JM110. In shake-flasks studies, JM110 (pBMS2000-PPFDH-PDHmod) was grown for 18 hours at 28° C., 250 rpm in MT5 medium (2.0% Yeastamine, 4.0% glycerol, 0.6% sodium phosphate [dibasic], 0.3% potassium phosphate [monobasic], 0.125% ammonium sulfate, 0.0256% magnesium sulfate [heptahydrate; added post-autoclaving from a sterile 1M solution], and 50 µg/ml kanamycin sulfate [added post-autoclaving from a filter-sterilized 50 mg/ml solution]). The optical density at 600 nm (OD$_{600}$) was recorded and cells sufficient to give a starting $OD_{600}$ of 0.35 were added to fresh MT5/kanamycin medium. Flasks were shaken at 250 rpm, 28° C. until the $OD_{600}$ was 0.8-1.0. Expression of both genes was induced by addition of filter-sterilized 1M isopropylthio-β-D galactopyranoside (IPTG) to a final concentration of 35 µM and the fermentation continued for 24-48 hours. Cells were pelleted by centrifugation at 6,500×g for 5 minutes, washed once with an equal volume of 50 mM ammonium formate pH 7.0, and repelleted. Cells were stored frozen at −20° C. or used immediately. The pellet was resuspended in 50 mM ammonium phosphate, pH 7.0 at 10 mL/g wet cell weight and sonicated 3×15 seconds using a Fisher Scientific Model 50 Sonic Dismembrator (Fisher Scientific, Pittsburgh, Pa.), power setting 15 with a microtip. Debris was pelleted by centrifugation at 13,000×g for 5 minutes at room temperature.

Expression was examined by sodium dodecyl sulfate-polyacrylamide gel electrophoresis (SDS-PAGE). One µL of the cell extract was mixed with 5 µL of 4× NuPAGE™ LDS buffer (Invitrogen) and brought up to 19 mL with distilled water. Samples were heated at 70° C. for 10 minutes. One mL of a 1M dithiothreitol solution was added to the mixture and 10 µL applied to a 10% NuPAGE™ Bis-Tris polyacrylamide mini-gel. Electrophoresis was carried out at 200 v for 50-60 minutes and the gel stained in a solution consisting of 0.1% (w/v) Coomassie Blue (Sigma), 40% (v/v) ethanol, and 10% (v/v) acetic acid. The gel, immersed in the stain, was heated in a microwave oven until boiling was evident, then shaken at 40 rpm on an orbital shaker for 15 minutes. The gel was washed thoroughly with deionized water and covered with destaining solution (GelClear™; Invitrogen). The solution was again heated just to the point of boiling and shaken gently for at least 2 hours. Two prominent bands at $M_r$ 43,000 and 40,000 were seen upon induction, corresponding to the expected molecular weight of the subunits of FDH and PDHmod. Samples were also found to possess both FDH and PDH activities when tested as described in Example 10. This recombinant E. coli strain was given the internal designation of SC 16496.

SC 16496 was subsequently fermented at 15- and 250-liter volumes. For a 15-liter fermentation, one vial containing 1 mL of frozen SC 16496 was thawed at room temperature and added to 1 liter of MT5 medium containing 50 µg/ml kanamycin in a 4-liter flask. The flask was incubated at 28° C., 250 rpm for 24 hours and transferred to 13 liters of MT5 medium (ingredients batched based on a final volume of 15 L) in a Braun fermentor. Kanamycin sulfate and magnesium sulfate heptahydrate sufficient to give a final concentration of 50 µg/ml and 0.0246%, respectively, were dissolved in 500 mL distilled water and filter-sterilized through a 0.2 micron cellulose acetate filtration unit. The solution was added to the tank, followed immediately by the inoculum. The initial $OD_{600}$ was ca. 0.35.

Fermentation operating parameters were as follows:
16 liter working volume
Temperature: 28° C.
Aeration: 1.0 vvm
Pressure: 690 mbar
Agitation: 500 rpm
Control pH at 6.8 with $NH_4OH$ as required Foaming was controlled by addition of UCON (a fluorocarbon solvent blend produced by Dow Chemical Company) on demand.

At $OD_{600}$ 0.8-1.0 (approximately two hours after inoculation), filter-sterilized IPTG (dissolved in 500 mL $dH_2O$) was added aseptically to give a final concentration of 35 µM. The fermentation continued for an additional 48 hours, whereupon the contents of the tank were subcooled to 10° C. Cells were collected by centrifugation and rinsed once with 0.1 vol 50 mM ammonium formate pH 7.0. The cell paste was placed into plastic containers and stored at −70° C. until needed.

For 250-L tanks, the inoculum was prepared as follows: 1 mL of frozen SC 16496 was thawed and added to 300 mL MT5 medium with 50 µg/ml kanamycin. The flask was grown at 28° C., 250 rpm for 24 hours. The $OD_{600}$ was determined and the appropriate volume of cells to give 80 OD units was removed and added to 250 mL fresh MT5 medium. The cells were aseptically added to 10 L of MT5/kanamycin medium in a Braun fermentor (initial $OD_{600}$~0.008) and grown under the Fermentation Operating Parameters disclosed supra for 16 hours. The culture was then transferred to 250 L of MT5 containing the appropriate concentrations of kanamycin and magnesium sulfate. Based on the 90 minute doubling time of SC 16496 under these conditions, 10 L of inoculum in 250 L should give a starting $OD_{600}$ of 0.30-0.35. Induction, growth, harvesting, and storage were carried out as described for the 15-L fermentation.

Example 8A

Telescoped production of (αS)-α-[[(1,1-dimethylethoxy)carbonyl]amino]-3-hydroxytricyclo[$3.3.1.1^{3,7}$]decane-1-acetic acid (Formula VI) from 3-hydroxy-α-oxotricyclo-[$3.3.1.1^{3,7}$]decane-1-acetic acid (Formula 11) through (αS)-α-amino-3-hydroxytricyclo[$3.3.1.1^{3,7}$]decane-1-acetic acid (Formula V) using an isolated PDH/FDH enzyme concentrate Step 1: Isolation of PDH/FDH enzyme concentrate Fermentation broth (30 liters) of Escherichia coli JM110 (pBMS2000-PPFDH-PDHmod) was obtained from a 4000 L tank fermentation and passed through a microfluidizer (Microfluidics model M-110Y, operating pressure 12,000-20,000 psi) (one pass) to release the activity from the cells keeping the temperature of the broth below 40°. The PDH/FDH activity of microfluidized broth was 32 IU/ML for PDH and 8 IU/ml for FDH.

To clarify the whole broth, 4.5 kg of Celite was added to well-stirred broth. Then 0.201 liters of 30% aq. polyethyleneimine was added and mixed for 30 minutes. The mixture was then filtered using a filter press (Ertel Alsop model 8-ESSC-10) and 18 liters of filtrate was obtained. The filter cake was washed with 12 liters of water to bring the volume back to 30 liters. The step yield was 97% activity recovery of PDH with an activity of 31 IU/ml and a FDH activity of 8 IU/ml.

The clarified broth was ultrafiltered through a 100,000 MWCO filter cassette (Millipore Pellicon 2 unit, polyethersulfone low protein binding cassette, 0.5 $m^2$ filter area). The circulation rate of the pump was 400 mL/min. The clarified filtrate was concentrated to 1.5 liters and gave an enzyme concentrate with PDH titer of 567 IU/ml and FDH titer of 136 IU/ml. The permeate was assayed and no activity was found. The overall enzyme activity recovery in the concentrate was 84%.

Step 2: Reductive Amination

3-Hydroxy-α-oxotricyclo-[$3.3.1.1^{3,7}$]decane-1-acetic acid (Formula II) (1.00 kg; 4.46 mol) was added to a 20 L vessel followed by water (5 L). The mixture was stirred and the pH was adjusted to pH~8 with 10N NaOH to give a solution. Darco KBB carbon (100 g) was added and the mixture was stirred for 5 minutes then filtered through a Buchner funnel with 5μ filter paper. The filter was washed with water (2×1 L) and the filtrates and washes were combined to give a clear solution.

With stirring, ammonium formate (0.562 Kg; 8.92 mol) was added and the pH was re-adjusted to ~7.5 with 10N NaOH. Nicotinamide adenine dinucleotide (2.65 g) and dithiothreitol (1.54 g) were added. When the solids had dissolved, a PDH/FDH enzyme concentrate was added (1.03 L; 500,000IU of PDH). The pH was re-adjusted to ~8.0 with 10N NaOH at ambient temperature.

The mixture was then warmed to ~40° C. and diluted to a total volume of 10 L with water. The pH was maintained at 7.7-8.3 while stirring over 42 hours. The resulting solution contained 0.955 Kg (95.1%) of the product (αS)-α-amino-3-hydroxytricyclo[3.3.1.1 $^{3,7}$]decane-1-acetic acid (Formula V).

Step 3: BOC-Protection

Di-tert-butyl dicarbonate (1.022 kg; 4.68 mol) was added to a portion of the solution of (αS)-α-amino-3-hydroxytricyclo[3.3.1.1$^{3,7}$]decane-1-acetic acid (Formula V) (477.5 g; 2.12 mol). This mixture was stirred at ambient temperature, with pH adjusted to and maintained at 10 with a pH stat titrator using 10N NaOH. The reaction was complete 4 hrs after Boc$_2$O addition when there was less than 1.0% starting material remaining.

The pH of the mixture was adjusted to 8 with 35% H$_2$SO$_4$ and i-PrOAc (5.0 L) was added to the mixture. The pH of the mixture was then adjusted to 2.0 with 35% H$_2$SO$_4$ and maintained at this pH for 5-10 min. Dicalite (250 g) was added; the mixture was stirred for ~10 min, and then filtered through a pad of Dicalite (250 g) on filter paper in a Buchner funnel. The Dicalite pad was further washed with 2.5 L i-PrOAc.

The filtrate was adjusted to pH 8 with 10N NaOH. After settling for 1 hr, the organic layer including interface was discarded. To the aqueous layer, i-PrOAc (7.5 L) was added. The mixture was acidified with 35% H$_2$SO$_4$ to pH~2, and then heated to and maintained at ~40° C. for 4 hours with mild stirring. The layers were separated and the organic extract was saved. The aqueous layer with interface was extracted with i-PrOAc (3.75 L) and the layers were again separated after 2 hrs at 40° C. The aqueous layer with interface was extracted again with i-PrOAc (3.75 L) and the layers were separated after 2 hrs at 40° C.

The combined organic extracts (~15 L) were concentrated by distillation to ~4.5 L. To this solution, heptane (~10 L) was then added over 10-15 min while the temperature was maintained at ~82-89° C. The reactor jacket temperature was set to 70° C. and maintained at this temperature for 1 hr. Crystallization occurred shortly after cooling. The reactor jacket temperature was then set at 40° C. and maintained at this temperature for 30 min.

The suspension was cooled down to ambient temperature, and then further cooled to 0-5° C. After one hour of stirring at 0-5° C., the product was filtered. The product was washed with heptane (2.5 L), then dried in vacuo at 40° C. to give 607.0 g (88% yield) of (αS)-α-[[(1,1-dimethylethoxy)carbonyl]amino]-3-hydroxytricyclo[3.3.1.1$^{3,7}$]decane-1-acetic acid (Formula VI).

Example 9

Reductive Amination using an Extract from Recombinant *Escherichia coli* SC16496 JM110[pBMS2000-PPFDH-PDHmod] (ATCC Deposit PTA-4520)

Recombinant *Escherichia coli* frozen cells (25 grams) were added to deionized water (sufficient to bring the final volume to 100 ml and containing 5 ml 1 M ammonium formate). After thawing, the cells were suspended using a Janke and Kunkel Ultra-turrax T8 homogenizer then adjusted to pH 7 with concentrated NH$_4$OH and cooled with crushed ice to give a 25% w/v cell suspension in 50 mM ammonium formate. Cells were disrupted by 2 passages through a microfluidizer at 12000 psi and cell debris was removed by centrifugation at 20,000×g and 4° C. 266 ml supernatant containing 2456 u (assay A) or 768 u (assay C) phenylalanine dehydrogenase and 8801 u formate dehydrogenase was added to a 1-L bottle.

A 266 ml solution was prepared containing ammonium formate (16.74 g, 0.2654 moles) and (3-hydroxy-adamantan-1-yl)-oxo-acetic acid (29.76 g, 0.1327 moles) and brought to pH 8.0 with 12.7 ml concentrated ammonium hydroxide. AND (372 mg, 0.561 mmoles) and dithiothreitol (81.8 mg, 0.530 mmoles) were added, then the solution was added to the bottle containing the *Escherichia coli* extract. The bottle was maintained at 400 on a shaker at 40 rpm. Concentrated ammonium hydroxide was added periodically to maintain pH 8.0 After 38 hours, the solution contained 31.5 grams (0.140 moles, 100% yield) (S)-amino-(3-hydroxy-adamantan-1-yl)-acetic acid as measured by HPLC analysis and no R-enantiomer of the amino acid.

Example 10

Reductive Amination using Freeze Dried Cells from Recombinant *Escherichia coli* SC16496 JM110[pBMS2000-PPFDH-PDHmod] (ATCC Deposit PTA-4520)

The solution contained in a final volume of 10.0 ml at pH 8.0 (pH adjusted with NH$_4$OH): 0.50 M ammonium formate, 0.237 M (3-hydroxy-adamantan-1-yl)-oxo-acetic acid, 1.00 mM AND, 1.00 mM dithiothreitol, and 975 mg freeze dried recombinant *Escherichia coli*. The cells were dried to 26% of the wet weight. Before drying the cells contained 65.04 units/g (assay A) phenylalanine dehydrogenase, (or 12.79 unit/g by assay C phenylalanine dehydrogenase), and 133.32 units/g formate dehydrogenase. The solution was incubated in a tightly sealed 50 ml Erlenmeyer flask at 40° C., 100 rpm for 3 days, then analyzed by HPLC. The solution contained 49.06 mg/ml (92.13.0% yield) (S)-amino-(3-hydroxy-adamantan-1-yl)-acetic acid.

Example 11

Transamination using Branched Chain Transaminase

A solution was prepared containing in a final volume of 1.0 ml in 50 mM potassium phosphate buffer, pH 8.0:0.10 M sodium glutamate, 0.05 M (3-hydroxy-adamantan-1-yl)-oxo-acetic acid (neutralized with 0.05 M NaOH), 0.1 mM pyridoxal phosphate, and 1 mg branched chain transaminase (Biocatalytics). The solution was incubated in a microfuge tube at 37° for 68 hours, then analyzed by HPLC. The solution contained 5.53 mg/ml (49.2% yield)(S)-amino-(3-hydroxyadamantan-1-yl)-acetic acid and 7.05 mg/ml remaining (3-hydroxy-adamantan-1-yl)-oxo-acetic acid.

Example 12

HPLC Assay of (S)-amino-(3-hydroxy-adamantan-1-yl)-acetic acid Enantiomeric Excess and Amount Samples were diluted with water to about 2 mg/ml concentration and placed in a boiling water bath for 1 minute to stop reactions and precipitate proteins. After cooling, the samples were filtered through 0.2 micron nylon filters into HPLC vials.

Two separation methods were used.

Method 1:
 column: Chiralpak WH 25×0.46 cm (Daicel Industries, Ltd.).
 mobile phase: 0.3 mM $CuSO_4$
 flow rate: 1 ml/minute
 column temperature: 50° C.
 detection: diode array detector (DAD) set at 240 nm
 injection volume: 10 μl
 S-enantiomer ((<aS)-<a-amino-3-hydroxytricyclo[3.3.1.1$^{3,7}$]decane-1-acetic acid) retention time: 79.9 minutes
 R-enantiomer retention time: 32.8 minutes Method 2:
 column: Regis Davankov Ligand Exchange 15×0.46 cm
 mobile phase: 25% methanol/75% 6 mM $CuSO_4$
 flow rate: 1 ml/minute
 column temperature: 40° C.
 detection: DAD set at 240 nm
 injection volume: 10 μl
 S-enantiomer (<aS)-<a-amino-3-hydroxytricyclo[3.3.1.1$^{3,7}$]decane-1-acetic acid) retention time: 3.2 minutes
 R-enantiomer retention time: 11.2 minutes
 Ketoacid (3-hydroxy-<a-oxotricyclo[3.3.1.1$^{3,7}$]decane-1-acetic acid) retention time: 5.2 minutes Example 13

Phenylalanine Dehydrogenase Assay A

Phenylalanine dehydrogenase assay A contained in 1 ml at 40° C.: 0.4 mM NADH, 5 mM sodium phenylpyruvate, 0.75M $NH_4OH$ adjusted to pH 8.75 with HCl. Absorbance decrease was monitored at 340 nm. Enzyme activity units were calculated as μmoles/minute based on the rates of absorbance change.

Example 14

Phenylalanine Dehydrogenase Assay B

Phenylalanine dehydrogenase assay B contained in 1 ml at 40° C.: 1 mM AND, 10 mM L-phenylalanine, 0.1 M $K_2HPO_4$ adjusted to pH 10.0 with 1 N NaOH. Absorbance increase was monitored at 340 nm. Enzyme activity units were calculated as μmoles/minute based on the rates of absorbance change.

Example 15

Phenylalanine Dehydrogenase Assay C

Phenylalanine dehydrogenase assay C contained in 1.0 mL at 40° C.: 0.4 mM NADH, 50 mM 3-hydroxy-<a-oxotricyclo[3.3.1.1$^{3,7}$]decane-1-acetic acid (dissolved in 1 equivalent NaOH solution), 0.75M $NH_4OH$ adjusted to pH 8.75 with HCl. Absorbance decrease was monitored at 340 nm. Enzyme activity units were calculated as μmoles/minute based on the rates of absorbance change.

Example 16

Formate Dehydrogenase Assay

The formate dehydrogenase assay contained in 1.0 ml at 40° C.: 1 mM AND, 100 mM ammonium formate, 100 mM potassium phosphate buffer, pH 8.0. Absorbance increase was monitored at 340 nm. Enzyme activity units were calculated as μmoles/minute based on the rates of absorbance change.

Example 17

Bromination of tricyclo[3.3.1.1$^{3,7}$]decane-1-acetic acid (Formula N) to α-bromotricyclo[3.3.1.1$^{3,7}$]decane-1-acetic acid (Formula O)

Solid tricyclo[3.3.1.1$^{3,7}$]decane-1-acetic acid (Formula N) (288 grams; 1.48 mole) was suspended in thionyl chloride (465 mL) in a 3-necked round bottomed flask, equipped with a condenser. Dimethylformamide (DMF;0.3 mL was added and the suspension was stirred at room temperature for 1.5 hours. Completion of the reaction was checked by gas chromatography. Solid NBS (307 g) was then added portionwise to the reaction mixture and the reaction mixture was heated to 60° C. The reaction was stirred for 3 hours while maintaining the temperature at 60 to 65° C. Monitoring by gas chromatography was performed to ensure the completion of the reaction. Heptane (900 mL) was added to the reaction mixture. Excess thionyl chloride was distilled off at 78-80° C. Water was then added cautiously (violent reaction) to quench the reaction (total volume 1050 mL). Heptane (500 mL) and water (600 mL) were then added and the aqueous layer was separated from the organic layer. The organic layer was washed with additional water (600 mL) and the aqueous layer was again separated from the organic layer. Additional water (150 mL) was added to the organic heptane layer and the heptane was distilled off from the aqueous layer. Specifically, 70 mL of water co-distilled with heptane. After distilling off the heptane, tetrahydrofuran (THF;1200 mL) was added to the aqueous layer and the resulting mixture was stirred vigorously at room temperature for 16 hours for slow hydrolysis. Monitoring via gas chromatography indicated the presence of some unreacted acid chloride. Addition water (150 mL) was then added to speed up the hydrolysis and the reaction was monitored by gas chromatography to ensure completion. The THF was then distilled off yielding a biphasic (water and oil) reaction mixture. Seeds were then added and the reaction was allowed to reach room temperature so that a heavy solid comes out. Water (250 mL) and acetonitrile (500 mL) were added to keep the suspension stirrable as the suspension was stirred for 2 hours at room temperature. The solid was then filtered off and washed with acetonitrile (2×250 mL). This filtrate contained the first crop of α-bromotricyclo[3.3.1.1$^{3,7}$]decane-1-acetic acid (Formula O); 264 grams with AP 95 in 66% yield after drying in vacuo at room temperature. The mother liquor (113 gram residue) was then triturated the residue with water and acetonitrile (250 mL/250 mL) for 1-2 hours at room temperature. The reaction was then filter and the solid dried to obtain a second crop of α-bromotricyclo[3.3.1.1$^{3,7}$]decane-1-acetic acid (Formula O); 64 grams with AP 90 in 16% yield.

Example 18

Preparation of α-bromo-3-hydroxytricyclo[3.3.1.1$^{3,7}$]decane-1-acetic acid (Formula Q) from α-bromotricyclo[3.3.1.1$^{3,7}$]decane-1-acetic acid (Formula O)

An Erlen-Meyer flask was charged with 315 ml of 95-98% $H_2SO_4$ and then cooled to 8° C. in an ice bath. $HNO_3$ (35 ml of 50% prepared by adding 50 ml of 70% $HNO_3$ to 30 ml of water) was then added to the flask while maintaining the mixture in an ice bath at 8° C. Solid α-bromotricyclo[3.3.1.1$^{3,7}$]decane-1-acetic acid (Formula O) (92 grams, 0.338 moles) was then added to the mixture in portions over approximately 30 to 60 minutes so that the temperature stayed under 28° C°. The reaction was then stirred while heating to 60° C. until a clear solution was obtained.

Progress of the reaction was monitored by either thin layer chromatography (TLC) or high performance liquid chromatography (HPLC). TLC was performed with a silica gel using ethyl acetate/methanol/hexanes at a ration of 9:1:10 with $KMnO_4$. HPLC was performed using an ODS column, C18 S-3 120A, 4.6×50 mm, a linear gradient of 10% acetonitrile/$H_2O$ to 100% acetonitrile in 7 minutes, and a flowrate of 2.5 ml/minute. The detection wavelength was 220 nm.

When the reaction was complete, the mixture was cooled to room temperature and maintained there for approximately 16 hours. Water (700 mL) was then added to quench the reaction until no brown gases evolved. The resulting slurry was cooled in an ice bath to approximately 5° C. and then filtered. The solid filtrate was washed with 200 mL of water and air dried to yield 90 grams of α-bromo-3-hydroxytricyclo[3.3.1.1$^{3,7}$]decane-1-acetic acid (Formula Q) as a light yellow solid (92% yield).

Example 19

Preparation of (<aS)-<a-amino-3-hydroxytricyclo[3.3.1.1$^{3,7}$]decane-1-acetic acid (Formula V) from α-bromo-3-hydroxytricyclo[3.3.1.1$^{3,7}$]decane-1-acetic acid (Formula Q)

α-Bromo-3-hydroxytricyclo[3.3.1.1$^{3,7}$]decane-1-acetic acid (Formula Q) (75 grams, 0.278 moles) was dissolved in 225 mL of 30% ammonium hydroxide (4.08 moles, 14.6 equivalents). The reaction mixture was then heated at 65° C. for 16 hours. The reaction mixture was then concentrated on a rotovap to a solid. EtOH (200 mL) was added to the concentrated solid and then re-concentrated on rotovap. The yield was 71 grams of a chiral mixture of hydroxytricyclo[3.3.1.1$^{3,7}$]decane-1-acetic acid (Formula V) as a yellow solid (90%).

Example 20

Resolution of hydroxytricyclo[3.3.1.1$^{3,7}$]decane-1-acetic acid (Formula V)

Boc protection of the chiral mixture of Example 19 was performed using Boc anhydride and sodium hydroxide in tetrahydrofuran. The resulting compound α-[[(1,1-dimethylethoxy)carbonyl]amino]-]3]hydroxytricyclo[3.3.1.1$^{3,7}$]decane-1-acetic acid (Compound R) (0.25M in EA, 80 ul,=6.52 mg) was mixed with chiral base ([1R,2S]-(−)-1,2-diphenylhydroxy ethylamine) (0.25M, 80 ul) in a vial and the mixture was evaporated to dryness in the SpeedVac. Solvent (200 ul) was added. The vial containing the mixture was placed on a shaker with heating at 50° C. for 1.5 hours. The mixture was then cooled to room temperature for crystallization of (αS)-α-[[dimethylethoxy)carbonyl]amino]-3-hydroxytricyclo[3.3.1.1$^{3,7}$]decane-1-acetic acid (Compound S).

Example 21

$ZnCl_2$-catalyzed adamantyl bromide (Formula A) coupling

A dry vessel was charged with 7.5 kg adamantyl bromide. Methylene chloride (22.5 liters) was then added at room temperature to dissolve the solid adamantane bromide. Dissolving is endothermic so before the next step, the temperature of the reaction mixture was allowed to return to 20° C. The reaction mixture was then charged with zinc chloride (1.05 kg) and stirred for approximately 5 minutes at 20° C. The reaction mixture was then charged with tris(trimethylsiloxy)-ethylene (15.3 kg) while maintaining the reaction temperature between 20 to 25° C. and the resulting mixture was stirred for 2 hours. Following this mixing, tris(trimethylsiloxy)-ethylene (5.10 kg) was added. During this addition, the temperature was maintained below 30° C. The reaction was maintained for another 12 to 15 hours at 20 to 25° C., at which time the reaction mixture was diluted with methylene chloride (15 liters) and cooled to 0 to 5° C. The reaction mixture was then treated, beginning in dropwise fashion, with half-saturated $NH_4Cl$ solution. During addition, the temperature was kept below 30° C. A thick suspension was obtained. To this suspension was added ethyl acetate (93.75 liters). The mixture was stirred vigorously for 15 minutes and the organic and aqueous phases were split. The organic layer was stored and the aqueous layer was washed twice with ethyl acetate (18.75 liters in each wash). The ethyl acetate washes and organic layer were then combined and washed with water (37.5 liters) followed by water half saturated with brine (37.5 liters). The organic layer was separated again and evaporated to form crystals. A solvent exchange to heptane was then performed at a final volume of 22.5 liters. The resulting suspension was cooled to 5 to 10° C. for 1 hour and the product <a-hydroxytricyclo[3.3.1.1$^{3,7}$]decane-1-acetic acid (Formula B) was obtained via filtration. Yield of <a-hydroxytricyclo[3.3.1.1$^{3,7}$]decane-1-acetic acid (Formula B) was 6.96 kg (33.11 mol, 95%).

Example 21A

Esterification of <a-hydroxytricyclo[3.3.1.1$^{3,7}$]decane-1-acetic acid (Formula B)

An inert atmosphere was first created in the reactor. The reactor was then charged with methanol (35.00 liters) followed by <a-hydroxytricyclo[3.3.1.1$^{3,7}$]decane-1-acetic acid (Formula B) (14.00 kg) to form a suspension. The suspension was cooled to 0 to 5° C. and acetyl chloride was added in a manner such that the temperature of the reaction mixture was kept between 5 and 10° C. After completion of the addition of acetyl chloride, the reaction mixture was warmed to 20 to 25° C. and stirred for 2 hours at 20 to 25° C. The reaction mixture was than concentrated under vacuum at 40° C. and a thin oil was obtained. The oil was dissolved in ethyl acetate (71.96 liters) and brought to room temperature. The resulting mixture was washed twice in water (28.78 liters each wash) and the organic and aqueous layers were separated after each wash. The organic layer was stored while the aqueous layers were combined and adjusted to pH 9.5 with 3 N NaOH solution. The combined aqueous layers were then extracted twice with ethyl acetate (14.39 liters with each extraction). The organic layers following each extraction were separated and combined with the stored organic layer. These combined organic layers were then washed with saturated sodium bicarbonate solution (28.78 liters) followed by brine (43.18 liters). All volatiles were then removed under vacuum at 40° C. and a colorless to slightly yellow oil which crystallized on standing was obtained. This oil contained 13.29 kg. (59.26 mol, 89%) <a-hydroxytricyclo[3.3.1.1 $^{3,7}$]decane-1-acetic acid, methyl ester (Formula C).

Example 22

Swern Oxidation of <a-hydroxytricyclo[3.3.1.1$^{3,7}$] decane-1-acetic acid, methyl ester (Formula C)

A three-necked flask (22 liters) was equipped with a mechanical stirrer, temperature probe and an addition funnel and purged with nitrogen overnight. Oxalyl chloride (500 ml, 5.73 mol) was then added followed by $CH_2Cl_2$ (8 liters). The resulting solution was cooled to −69° C. with an acetone/dry ice bath. A solution of dimethylsulfoxide (DMSO; 700 ml, 9.86 mol) was then slowly added over approximately 30 minutes while keeping the internal temperature below −60° C. The solution was stirred for 20 minutes while maintaining the temperature at −60 to −70° C. A solution of <a-hydroxytricyclo[3.3.1.1$^{3,7}$]decane-1-acetic acid, methyl ester (Formula C) (990 grams, 4.42 mol) in $CH_2Cl_2$ (1.7 liters) was then slowly added over approximately 30 minutes while keeping the internal temperature below −60° C. The resulting solution was stirred for 30 minutes. $NEt_3$ (3 liters, 21.5 mol) was then added to form a heavy slurry of triethylamine hydrochloride salt. The reaction mixture was warmed to room temperature and water (1 liter) was added to dissolve triethyl ammonium salt (TEA salt). The reaction mixture was then transferred to a round bottom flask, and concentrated down to remove dichloromethane (DCM) and $NEt_3$. EtOAc (12 liters) was added and the resulting aqueous and organic layers were split. The organic layer was washed three times with water (2 liters each wash) followed by a brine wash (2 liters). The organic phase was then dried over anhydrous $Na_2SO_4$ with evaporation to produce a slight yellow solid of <a-oxotricyclo [3.3.1.1$^{3,7}$]decane-1-acetic acid, methyl ester (Formula D). Yield was approximately 104%.

Example 23

Hydroxylation of <a-Oxotricyclo[3.3.1.1$^{3,7}$]decane-1-acetic acid, methyl ester (Formula D) to 3-hydroxy-<a-oxotricyclo[3.3.1.1$^{3,7}$]decane-1-acetic acid, methyl ester (Formula I)

An Erlenmeyer flask was charged with 95 to 98% $H_2SO_4$ (495 ml) and cooled in an ice bath to 8° C. $HNO_3$ (47.5 ml at 50% prepared by adding 50 ml of 70% $HNO_3$ to 30 ml of water) was then added to the flask and the mixture was again cooled to 8° C. in the ice bath. Solid <a-oxotricyclo[3.3.1.1$^{3,7}$]decane-1-acetic acid, methyl ester (Formula D)(100 grams, 0.45 moles) was slowly added to the mixture in portions over 30 to 60 minutes to maintain a temperature less than 28° C. The reaction mixture was stirred while cooling in the ice bath. Progress of the reaction was monitored by either thin layer chromatography (TLC) or high performance liquid chromatography (HPLC). For TLC, a silica gel was used and the solvent was EtOAc/MeOH/Hexane (9/1/10); $KMnO_4$. For HPLC, a 4.6×50 mm, C18, 3 micron, 120 angstrom column was used with a gradient of 10% acetonitrile/$H_2O$ to 100% acetonitrile in 7 minutes at a flow rate of 2.5 ml/minute. The monitoring wavelength was 200 nm. When the reaction was complete (after approximately 1 hour), the reaction was quenched by addition to cold water (1.5 liters) and EtOAc (500 ml). Additional water and EtOAc (500 ml each) were added to aid in separation of the aqueous and organic layers. The aqueous layer was then extracted with 3 aliquots, 500 ml each, of EtOAc. The organic layers were combined and washed with brine (400 ml). The washed organic layer was then concentrated under reduced pressure to 130 grams of a yellow oil residue containing 3-hydroxy-<a-oxotricyclo [3.3.1.1$^{3,7}$]decane-1-acetic acid, methyl ester (Formula I).

Example 24

Hydrolysis of 3-hydroxy-<a-oxotricyclo[3.3.1.1$^{3,7}$] decane-1-acetic acid, methyl ester (Formula I) to 3-hydroxy-<a-oxotricyclo[3.3.1.1$^{3,7}$]decane-1-acetic acid (Formula II)

The yellow oil residue of Example 23 was dissolved in tetrahydrofuran (300 ml) and cooled in a ice bath to 5° C. One liter of 1 N sodium hydroxide was added slowly to the solution to adjust the pH to approximately 7 while maintaining the temperature below 30° C. An additional 500 ml of 1N NaOH was then added to adjust the pH to approximately 14. The reaction mixture was then stirred while cooling in an ice bath and the progress was monitored by TLC or HPLC as described in Example 23. When the reaction was complete after approximately 30 minutes, EtOAc (500 ml) was added and the aqueous and organic layers were separated. The aqueous layer was washed with another 500 ml of EtOAc. The aqueous layer was acidified with concentrated HCl. When the solution reached pH 7, EtOAc (500 ml) was added followed by more concentrated HCl until the pH reached 0.7. Total concentrated HCl added was 150 ml. The aqueous layer was then extracted with EtOAc (4×400 ml) and the combined organic layers were washed with 400 ml of water followed by 400 ml of brine. The washed organic layer was then dried with $MgSO_4$ and concentrated. Yield was 88 grams of a light yellow solid. Dissolution of this solid in 100 ml EtOAc and 300 ml heptane with stirring for 30 minutes followed by filtration and air drying yielded 85 grams of a tan solid (85% 3-hydroxy-<a-oxotricyclo[3.3.1.1$^{3,7}$]decane-1-acetic acid (Formula II)).

Example 25

Preparation of Adamantan-1-yl-dichloro-acetic acid methyl ester (Formula VII)

A 2-liter three-necked flask equipped with a mechanical stirrer, thermometer, condenser, pressure equalizing addition funnel and an argon inlet was charged with zinc dust (78.0 g, 1.19 mol) followed by the addition of anhydrous tetrahydrofuran (400 ml). To this mixture was added 1,2-dibromoethane (2 ml) to activate the zinc. The resulting mixture was heated at a gentle reflux for 25 minutes. After cooling to −55° C., a solution of methyl trichloroacetate (100.3 g, 0.565 mol) and chlorotrimethylsilane (80 ml, 0.648 mol) was added at a rate to maintain the reaction temperature at −55 to −60° C. (1 hour required). After the addition was complete, the mixture was allowed to stir at room temperature for approximately 90 minutes. The resulting mixture was diluted with heptane (700 ml) and filtered under nitrogen through a Celite 545 pad. The filtercake was washed with additional heptane (1×300 ml, 3×200 ml). The filtrate was then concentrated at reduced pressure on a rotary evaporator (approximately 10-15 mm Hg with a 22-27° C. water bath) to give crude (2,2-dichloro-1- methoxy-vinyloxy)-trimethylsilane as a dense oil (129.2 g). Quantitative proton NMR indicates this crude material contains 0.389 mol (68.8%) of (2,2-dichloro-1-methoxy-vinyloxy)-trimethylsilane.

A 1 liter flask equipped with an argon inlet was charged with crude (2,2-dichloro-1-methoxy-vinyloxy)-trimethylsilane (129.1 g, approximately 0.389 mol) and anhydrous dichloromethane (100 ml). To the resulting solution was added 1-bromoadamantane (75.2 g, 0.349 mol) and anhydrous zinc chloride (6.56 g, 48 mmol). The resulting mixture was allowed to stir at room temperature overnight. The resulting red-brown mixture was diluted with heptane (600 ml) and water (300 ml). The organic layer was separated and washed with water (2×100 ml), 1 N sodium bicarbonate (3×150 ml), and water (2×200 ml). The resulting solution was filtered though a pad of Celite 545 and filtrate was concentrated at reduced pressure to give a colorless solid. This material was dissolved in boiling methanol (250 ml). The resulting solution was allowed to cool to room temperature for 1 hour. After cooling to approximately 5° C. for 2 hours, the solid was collected by filtration and washed with cold methanol:water (94:6; 4×50 ml) to give adamantan-1-yl-dichloro-acetic acid methyl ester (Formula VII) as a colorless solid: 75.0 grams (77.3% based on 1-bromoadamantane); mp 76.3° C.

| Elemental analysis: | $C_{13}H_{18}Cl_2O_2$: |
|---|---|
| Calculated: | C, 56.33; H, 6.55; Cl, 25.58% |
| Found: | C, 56.49; H, 6.59; Cl, 25.72% |
| $^1$H NMR (500.16 MHz, CDCl$_3$)δ | 3.855 (s, 3H), 2.069 (br s, 3H), 1.866 (d, J=2.75Hz, 6H), 1.683, 1.612 (AB q, J=12.1Hz) ppm |
| $^{13}$C NMR (127.78 MHz, CDCl$_3$) δ | 166.130, 95.805, 53.969, 43.980, 36.842, 36.256, 28.309 ppm |

Example 26

Preparation of Dichloro-(3-hydroxy-adamantan-1-yl)-acetic acid methyl ester (Formula VIII)

Preparation of 10 N HNO$_3$: A 100 mL volumetric flask was charged with conc. HNO$_3$ (88.25 g, ~62.58 mL, ~1.0 mole) and cooled in an ice bath. Water (35 mL) was added. After the heat of mixing had dissipated, the solution was allowed to warm to room temperature. The flask was then made up to the mark with water to give 10 N HNO$_3$ A 250 mL three-necked flask equipped with a thermocouple thermometer was charged with conc. H$_2$SO$_4$ (103 g, ~56 mL,). After cooling to 0.4° C. in an ice bath, 10 N HNO$_3$ (5.68 mL, 56.8 mmol) was added over ~30 minutes. When the temperature of this acid mixture was lowered to ~1.0° C., the cold bath was removed. Adamantan-1-yl-dichloro-acetic methyl ester of formula VII (15.0 g, 54.11 mmol; ground lightly in mortar/pestle to break up large chunks/crystals) was added portionwise (1.25 g every 10 minutes; 1 hr 50 minute addition time). After ~5 hours the reaction mixture was a clear, pale yellow solution.

After stirring for ~24 hours the reaction mixture was a very pale yellow solution. A four-necked Morton flask (1 L) equipped with a mechanical stirrer and thermocouple thermometer was charged with water (250 mL) and urea (8.0 g, 0.133 mole, ~2.34 equivalents relative to HNO$_3$). To the resulting solution was added ethyl acetate (230 mL). Resulting biphasic mixture was cooled to ~1.0° C. in an ice bath. The reaction mixture from above was added, over ~15 minutes, to the cold EtOAc/water/urea mixture. The transfer was completed using additional ethyl acetate and water (~50 mL of each). After stirring for ~45 minutes, the cold bath was removed and the mixture was allowed to warm with stirring. After stirring for 4.5 hours (from start of quench), the resulting mixture was transferred to a separatory funnel (1 L) using additional ethyl acetate (~100 mL) to complete the transfer. The aqueous fraction was removed and extracted with ethyl acetate (1×80 mL). The organic fractions were combined and washed with water (2×90 mL), 1 N NaHCO$_3$ (4×90 mL), and brine. After drying over anhydrous magnesium sulfate, the solvent was removed at reduced pressure to give dichloro-(3-hydroxy-adamantan-1-yl)-acetic acid methyl ester of Formula VIII as a nearly colorless solid: 15.67 g (98.7% crude yield). This crude material can be used to prepare dichloro-(3-hydroxy-adamantan-1-yl)-acetic of Formula IX without purification. If desired, however, the crude material (15.65 g) can be recrystallized from methanol (102 mL) and water (85 mL) to afford a fluffy cotton-like solid (mp 114.8-115.0° C.) with 91% recovery.

| Elemental analysis: | $C_{13}H_{18}Cl_2O_3$: |
|---|---|
| Calculated: | C, 53.25; H, 6.18; Cl, 24.18% |
| Found: | C, 53.24; H, 6.24; Cl, 24.31% |
| $^1$H NMR (500.16 MHz, CDCl$_3$) δ | 3.857 (s, 3H), 2.298 (br m, 2H), 1.824 (s, 2H), 1.793 (d, 4H, =2.75Hz), 1.682, 1.629 (br AB q, 4H), 1.529 (m, 3H) ppm |
| $^{13}$C NMR (127.78 MHz, CDCl$_3$)δ | 165.929, 94.281, 68.932, 54.150, 44.47 8, 44.529, 44.020, 35.750, 34.759, 30.149 ppm |
| Lab HPLC: | |
| YMC ODS-A S3 120 Å (4.6 × 50 mm), λ = 200 nm, 2.5 ml/minute | |
| Solvents: | A = 0.2% H$_3$PO$_4$ in water |
| | B = 90% CH$_3$CN in water |
| Gradient: | 20% A to 100% B over 10 minutes |

| Retention Time | Area % | Identity |
|---|---|---|
| 2.06 minutes | 1.19 | unknown |
| 4.54 minutes | 98.16 | dichloro-(3-hydroxy-admantan-1-yl)-acetic acid methyl ester |
| 5.09 minutes | 0.65 | unknown |
| 8.35 minutes | | adamantan-1-yl-dichloro-acetic methyl ester |

Example 27

Preparation of Dichloro-(3-hydroxy-adamantan-1-yl)-acetic acid (Formula IX)

A 500 ml round-bottomed flask was charged with methanol (200 ml) and 1 N NaOH (194 ml, 194 mmol, approximately 1.36 equivalents relative to input dichloro-(3-hydroxy-adamantan-1-yl)-acetic acid methyl ester (Formula VIII)). The resulting solution was cooled in an ice bath until the temperature was <9° C. The cold bath was removed and dichloro-(3-hydroxy-adamantan-1-yl)-acetic acid methyl ester (Formula VIII)(41.68 g, 142.1 mmol) was added. The resulting suspension was allowed to stir at ambient temperature under argon. After stirring for approximately 6 hours, an additional portion of methanol (10 ml) was used to rinse down the vessel walls. After stirring for approximately 17 hours, the reaction mixture was filtered to remove a small amount of particulate material. The resulting solution was transferred to a 2-liter three-necked flask equipped with a mechanical stirrer. Water (900 ml) was used to dilute the reaction mixture and to compete the transfer. The resulting solution was acidified by the addition of concentrated HCl (38 ml, approximately 456 mmol). A white solid quickly formed. The mixture was gently stirred for approximately 20 minutes and then placed in an ice bath. After gently stirring for approximately 90 minutes, the stirrer was stopped and the mixture was allowed to stand in the ice bath for an additional 2 hours. The resulting suspension was filtered and the filtercake was washed with ice cold water. The bulk of the water was removed from the solid by pulling air through the filtercake. The material was then dried under vacuum at ambient temperature for 22 hours to give dichloro-(3-hydroxy-adamantan-1-yl)-acetic acid (Formula IX) as a colorless powdery solid: 39.19 grams (98.7% yield); mp 238° C. (dec).

| Elemental analysis: | $C_{12}H_{16}Cl_2O_3$: |
|---|---|
| Calculated: | C, 51.63; H, 5.77; Cl, 25.40% |
| Found: | C, 51.43; H, 5.74; Cl, 25.48% |

| Lab HPLC: | |
|---|---|
| YMC ODS-A S3 120 Å (4.6 × 50 mm), λ 200 nm, 2.5 ml/minute | |
| Solvents | A = 0.2% $H_3PO_4$ in water |
| | B = 90% $CH_3CN$ in water |
| Gradient: | 20% A to 100% B over 10 minutes |

| Retention Time | Area % | Identity |
|---|---|---|
| 0.53 minutes | 0.95 | unknown |
| 2.65 minutes | 97.27 | dichloro-(3-hydroxy-adamantan-1-yl)-acetic acid |
| 4.54 minutes | | dichloro-(3-hydroxy-adamantan-1-yl)-acetic acid methyl ester |

$^1$H NMR (500.16 MHz, $CD_3OD$) δ  2.258 (br s, 2H), 1.858 (s, 6H), 1.674, 1.615 (br AB q, J=l 1.54Hz, 4H)), 1.588-1.526 (m, 2H) ppm
$^{13}$H NMR (125.77 MHz, CD30D)δ  167.957, 96.356, 69.322, 48.070, 45.360, 44.794, 37.050, 36.039, 31.631 ppm

Example 28

Preparation of 3-Hydroxy-<a-oxotricyclo[3.3.1.1$^{3,7}$]decane-1-acetic acid (Formula II)

A 500 ml three-necked flask was charged with dichloro-(3-hydroxy-adamantan-1-yl)-acetic acid (Formula IX) (38.67 g, 138.5 mmol). To this material was added water (160 ml) and 1 N NaOH (138 ml, 138 mmol; 1 N NaOH was used to generate the sodium salt of dichloro-(3-hydroxy-adamantan-1-yl)-acetic acid to avoid foaming problems which would occur with solid $NaHCO_3$) to give a hazy solution. To this solution was added solid $NaHCO_3$ (29.10 grams, 346 mmol, 2.50 equivalents). After the $NaHCO_3$ was added the reaction mixture became a suspension as the sodium salt of dichloro-(3-hydroxy-adamantan-1-yl)-acetic acid was forced from solution. The reaction vessel was fitted with a reflux condenser/argon inlet and heated to approximately 80° C. After heating for approximately 6 hours the mixture was allowed to cool to room temperature. The reaction mixture (pH 7.22) was carefully acidified ($CO_2$ evolution) to pH 0.15 by the addition of concentrated HCl (32 ml required). The resulting mixture was extracted with ethyl acetate (4×300 ml). The aqueous layer (pH 0.37) after the first extraction with ethyl acetate was lowered to pH 0.18 by the addition of concentrated HCl (approximately 2 ml). The ethyl acetate fractions were combined and washed with brine (100 ml). After drying over anhydrous magnesium sulfate, the solvent was removed at reduced pressure to give 3-hydroxy-<a-oxotricyclo [3.3.1.1$^{3,7}$]decane-1-acetic acid (Formula II) as a colorless granular solid: 30.77 gram (99%).

| Elemental analysis: | $C_{12}H_{16}O_4$: |
|---|---|
| Calculated: | C, 64.27; H, 7.19% |
| Found: | C, 64.30; H, 7.13% |
| $^1$H NMR (500.16 MHz, $D_2O$) δ | 2.288 (br s, 1.33H), 2.227 (br s, 0.67H), 1.819-1.575 (m, 12H) ppm - partial hydrate |
| $^{13}$C NMR (125.77 MHz, $D_2O$) δ | 207.704, 174.583, 169.608, 98.109, 69.618, 68.830, 47.538, 43.716, 43.251, 43.190, 42.907, 42.563, 36.073, 34.677, 34.232, 30.006, 29.865 ppm - partial hydrate |

| Lab HPLC: | | |
|---|---|---|
| YMC ODS-A S3 120 Å (4.6 × 50 mm), λ = 200 nm, 2.5 ml/minute | | |
| Solvents: | A = 0.2% $H_3PO_4$ in water | |
| | B = 90% $CH_3CN$ in water | |
| Gradient: | 10% A to 60% B over 10 minutes | |

| Retention Time | Area % | Identity |
|---|---|---|
| 1.39 minutes | 100% | 3-hydroxy-<a-oxotricyclo[3.3.1.1$^{3,7}$]decane-1-acetic acid |
| 4.95 minutes | | dichloro-(3-hydroxy-adamantan-1-yl)-acetic acid |

Example 28A

Preparation of 3-Hydroxy-<a oxotricyclo-[3.3.1.1$^{3,7}$]decane-1-acetic acid (Formula II) employing a one pot procedure A 250-mL three-necked flask equipped with a pressure equating addition funnel and argon inlet was charged with dichloro-(3-hydroxy-adamantan-1-yl)acetic acid methyl ester (Formula VIII), prepared as described in Example 26 (15 g, 51.16 mmol) followed by the addition of tetrahydrofuran (30 mL, instabilized). After stirring for several minutes, the bulk of the Formula VIII methyl ester dissolved to give a hazy solution. To this solution was added distilled water (30 mL) and a loose suspension formed. The addition funnel was charged with 1N NaOH (69 ml, 69 mmol, ~1.35 eq relative to Formula VIII compound input). NaOH was added dropwise over 70 minutes to give a nearly colorless solution which was allowed to stir at ambient temperature.

HPLC analysis at ~16 hours showed the hydrolysis of the Formula VIII compound complete. The reaction mixture, a clear colorless solution with a pH of 13.24, was adjusted to pH 7.40 by the addition of ~6NHCl (2.8 mL). Solid $NaHCO_3$ (11.2 g, 0.133 mol., 2.60 eq) was added to form a suspension.

HPLC analysis after heating for 4 hr 15 min shows the reaction to be complete. After heating for 5 hours, the heat source was removed and the reaction mixture (clear, colorless solution) was allowed to cool. After cooling to room temperature, the reaction mixture was stored in a refrigerator (+4° C.) for 4 days.

After storage in the cold for 4 days the reaction mixture was still a clear colorless solution and HPLC analysis shows little, if any, change upon storage. After warming to room temperature, the mixture (pH 7.77) was acidified to pH 0.20 by the careful addition of conc. HCl (11 mL required, $CO_2$ evolution; at pH 1.40 a colorless solid began to precipitate). The resulting suspension was extracted with EtOAc (×4, ~500 mL total volume; HPLC analysis performed on aqueous fraction after each EtOAc extraction). The aqueous layer (pH 0.38) after the 1$^{st}$ EtOAc extraction was adjusted to pH 0.18 by the addition of conc. HCl (~1.6 mL required). The aqueous layer (pH 0.37) after the 2$^{nd}$ EtOAc extraction was adjusted to pH 0.17 by the addition of conc. HCl (~0.8 mL required). The aqueous layer required no additional pH adjustment after the remaining EtOAc extractions (extraction #3, pH 0.19; extraction #4, pH 0.19). The organic fractions were combined. After drying (MgSO$_4$), the solvent was removed at reduced pressure to give crude title Formula II compound as a nearly colorless, granular solid which was dried under vacuum (pump) for 16 hours: 11.42 g (99.53% yield); HPLC, 100% (area %).

| Elemental analysis: | C$_{12}$H$_{16}$Cl$_2$O$_3$ [55465-020-31, TR46373] |
|---|---|
| Calculated: | C, 64.27%; H, 7.19% |
| Found: | C, 64.19%; H, 7.09% |

Crude Formula II compound (5.0 g) was dissolved with heating to ~85° C. in distilled water (19 mL), then removed from the heat source and allowed to cool. At ~53° C., the material began to crystallize. After standing at room temperature for ~2 hours, the solid was collected by filtration and washed with ice cold water. The bulk of the water was removed by pulling nitrogen through the filtercake. The material was then dried under vacuum (pump) for 17 hours to give title Formula II compound as large, colorless needles: 4.33 g (86.6% recovery); mp 164.5-165.6° C. (on Mettler FP800 system); HPLC, 100% (area %).

| Elemental analysis: | C$_{12}$H$_{16}$Cl$_2$O$_3$ [55465-023-15, TR46905] |
|---|---|
| Calculated: | C, 64.27%; H, 7.19% |
| Found: | C, 64.42%; H, 7.04% |

Example 29

Esterification of L-pyroglutamic acid (Formula E) to form L-pyroglutamic acid ethyl ester (Formula F)

A reaction vessel was charged with ethanol (49.0 liters) and cooled to –5° C. The reaction vessel was then charged with thionyl chloride (4.97 kg) in a manner so that the temperature of the mixture did not exceed 0C. After complete addition of the thionyl chloride, the mixture was cooled again to –5° C. and L-pyroglutamic acid (Formula E) was added portionwise so that the temperature was maintained between 0 and –5° C. during the addition. Following addition of the acid, the reaction mixture was heated to 20 to 25° C. and stirred for 5 hours. The reaction mixture was then evaporated under vacuum (T max 45° C.) to approximately 15% of its original volume. The remaining oil was then dissolved in toluene (49 liters). The toluene solution was then cooled to approximately 10° C. and triethyl amine (8.45 kg) was added slowly so that the maximum temperature was between 20 and 25° C. The resulting suspension was stirred for 30 minutes and then filtered. The filter cake was washed with toluene (about 5 liters). The filtrate was reduced at 50° C. under vacuum to a total volume of about 10 liters. Crystallization was initiated by slow addition of cyclohexane (8 liters) at 50° C. and subsequent cooling to approximately 30° C. After seed formation the mixture was cooled to 20 to 25° C. and charged with a second 8 liter portion of cyclohexane. The mixture was then cooled to 6 to 8° C., stirred for one hour, and the resulting crystals were filtered off. The crystals were washed twice with cyclohexane (4 liters each wash). The yield was 4.89 kg (82%) L-pyroglutamic acid ethyl ester (Formula F) as colorless needles.

Example 30

BOC-Protection of L-Pyroglutamic acid ethyl ester (Formula F)

The L-pyroglutamic acid ethyl ester (Formula F)(5.00 kg) was dissolved at room temperature in toluene (24.97 liters). 4-Dimethlyaminopyridine (0.19 kg) was then added to the solution. The reaction mixture was then charged with a solution of BOC-anhydride (7.29 kg) dissolved in toluene (24.97 liters) in a manner so that the reaction temperature did not exceed 25° C. After complete addition, the reaction temperature was stirred for three hours at 25° C. The reaction mixture was then charged with half saturated NaHCO$_3$-solution (49.94 liters) and stirred vigorously for 10 minutes before separating the organic and aqueous phases. The separated organic layer was washed twice with water (24.97 liters each). The organic layer was then evaporated from solvent under vacuum at a maximum of 50° C. The remaining colorless to slight yellowish oil crystallized on standing. The theoretical yield was 8.18 kg, (31.81 mol) of the (5S)-2-oxopyrrolidine-1,5-dicarboxylic acid, 1-(1,1-dimethylethyl), 5-ethyl ester (Formula G).

Example 31

SuperHydride Reduction and Elimination

The (5S)-2-oxopyrrolidine-1,5-dicarboxylic acid, 1-(1,1-dimethylethyl),5-ethyl ester (Formula G)(4.80 kg) was dissolved in toluene (30.97 liters; Kf max 0.01% water) and cooled to –50° C. This solution was charged with SuperHydride (LiEt$_3$BH 1 M in THF; 19.96 liters) in a manner so that the reaction temperature did not exceed –45° C. After complete addition, the mixture was stirred at –45 to –50° C. for 30 minutes. N-ethyldiisopropylamine (DIPEA; 14.47 liters) was then added to the reaction mixture in a manner so that the temperature did not exceed –45° C. Dimethyaminopyridine (0.030 kg) was added as a solid to the mixture. The reaction mixture was then charged with trifluoroacetic anhydride (TFAA) (4.70 kg) in a manner so that the reaction temperature did not exceed –45° C. After complete addition, the reaction mixture was warmed to 20 to 25° C. within one hour and kept for an additional 2 hours at this temperature. The reaction mixture was then cooled to 0° C. and slowly charged with water (48.00 liters) so that the reaction temperature did not exceed 5° C. Aqueous and organic phases were then separated and the organic phase was again washed with 48 liters of water (0 to 5° C.). The organic later was then evaporated and degassed at 40° C. A yellowish oil was obtained with a yield of 4.5 kg (18.66 mol, 100%) of the 4,5-dihydro-1H-pyrrole-1,5-dicarboxylic acid, 1-(1-dimethylethyl), 5-ethyl ester (BOC-DHPEE)(Formula III).

Example 32

Hydrolysis of BOC-DHPEE (Formula III)

A solution prepared from 4,5-dihydro-1H-pyrrole-1,5-dicarboxylic acid, 1-(1,1-dimethylethyl),5-ethyl ester (BOC-DHPEE)(Formula III)(6.00 kg) and ethanol (24.00 liters) was cooled to 0 to 5° C. and slowly treated at this temperature with a solution of lithium hydroxide hydrate (2.09 kg) in water (20.87 liters) to produce a turbid solution. This turbid solution was then warmed to 20 to 25° C. and stirred for 2 hours at this temperature. The reaction mixture was then evaporated to a volume of approximately 10.5 liters at a maximum temperature of 40° C. under vacuum and charged with water (24.00 liters) and t-butylmethyl ether(TBME or MTBE), (24 liters) and mixed for 10 minutes. The resulting organic and aqueous phases were separated and the aqueous phase was charged again with 24 liters of TMBE. This mixture was then cooled to 5 to 10° C., and the pH was adjusted to 2.3 to 2.3 using $H_3PO_4$ 85%-water (1:4) while being vigorously stirred. The temperature was maintained during this process at 5 to 10° C. for stability. The resulting organic and aqueous layers were separated. The organic layer was stored and the aqueous layer was again extracted with 24 liters of pre-cooled TBME at 5 to 10° C. The resulting organic layer was combined with the stored organic layer and charged with diisopropylethylamine (DIPEA) (4.82 kg). The solution was then evaporated and degassed at a maximum temperature of 30° C. under vacuum. The yield was 7.84 kg (22.88 mol, 92%) [N-BOC dehydroproline * DIPEA (BOC-DHP)].

Example 33

Amide Formation on BOC-DHP

BOC-DHP, synthesized by saponification as described in Example 32 may contain water. Therefore an azeotropic distillation with toluene was applied prior to running the reaction. However, due to the excess of reagents, calculation of raw materials was based on the amount of BOC-DHP prior to removing any water. For azeotropic distillation, BOC-DHP was diluted with toluene to an approximate 30% solution. Toluene was removed under vacuum at 40° C. Treated BOC-DHP (6.00 kg) was then dissolved in THF (48.0 liters). The solution was charged with DIPEA (2.26 kg) and the reaction mixture was cooled to −20 to −25° C. Mesyl chloride (3.01 kg was then added slowly. During this addition, DIPEA hydrochloride precipitates. The resulting suspension was then stirred for 2 hours at −20° C. followed by saturation with ammonia via a sub-surface gas inlet. While adding the ammonia, the reaction was heated to 0° C. After saturation, the reaction mixture was heated to 20° C. and stirred for 3 hours. Following stirring, the reaction mixture was filtered to remove hydrochloride. The filter cake was washed with THF (12 liters) in several portions. The filtrate was concentrated under vacuum at a maximum temperature of 40° C. and then dissolved in methylene chloride (33.33 liters). The solution was washed with water (26.66 liters). The resulting organic and aqueous phases were separated and the aqueous phase was extracted twice with methylene chloride (20 liters each). The resulting organic layers were combined and concentrated under vacuum and degassed to remove any excess Hünigs base. The yield was 3.35 kg (15.77 mol, 90%) of (5S)-5-aminocarbonyl-4,5-dihydro-1H-pyrrole-1-carboxylic acid, 1-(1,1-dimethylethyl)ester (BOC-DHPA)(Formula IV).

Example 34

Cyclopropanation of (5S)-5-aminocarbonyl-4,5-dihydro-1H-pyrrole-1-carboxylic acid, 1-(1,1-dimethylethyl) ester (Formula IV)

A first reactor, Reactor A, was charged with BOC-DHPA (Formula IV)(4 kg) dissolved in methylene chloride (18.0 liters) and maintained at 20° C. A second reactor, Reactor B, was charged with methylene chloride (18.00 liters) and cooled to −30° C. Reactor B was then charged with dimethoxy ethane (DME) (3.36 kg), followed by a 30% solution of diethyl zinc (15.36 kg) in toluene, while maintaining the temperature between −30 and −25° C. Reactor B was then charged with diiodo methane (19.99 kg) while maintaining the reaction temperature between −30 and −25° C. After complete addition of the diiodo methane, the mixture was stirred for 45 minutes at −30 to −25° C. This mixture was then charged to Reactor A via a cooled pipe (−20 to −25° C. ). Charging was performed slowly in portions of approximately 5% so that the reaction temperature of Reactor A was maintained between 22 and 24° C. until the reaction was completed. Following completion of the reaction, the mixture of Reactor A was cooled to 5 to 10° C. The reaction mixture was then slowly charged with saturated bicarbonate solution (21.6 liters) in a manner so that the reaction temperature did not exceed 15° C. Following this addition, the reaction mixture was stirred for at least one hour while a precipitate formed. The suspension was filtered. The resulting filter cake was transferred back to the vessel, slurried again with methylene chloride (14.4 liters) for 30 minutes; and re-filtered. Following this second filtration, the filter cake was washed with addition methylene chloride (7.2 liters). The filtrates were then separated into aqueous and organic phases and the organic phase was washed with half saturated brine (21.6 liters). Solvent was then removed by vacuum at a maximum temperature of 30° C. and exchanged by heptane. A slurry of crude product in heptane was obtained. Final volume of the suspension after solvent exchange was 14.4 liters. The crude product was isolated by filtration. The filtercake was washed with heptane (2.9 liters) and then dried under vacuum to a constant weight. The crude yield was 2.76 kg (12.2 mol, 72%) [1S-(1<a,3<b,5<a]-3-aminocarbonyl)-2-azabicyclo[3.1.0] hexane-2-carboxylic acid, 1,1-dimethylethyl ester (Formula H). To purify, the crude material is slurried in 8-fold amount of a 1:1 mixture of butyl acetate/heptane at 20 to 22° C. for 4 hours. The material was filtered and the filtercake was washed with an approximate 1-fold amount of heptane. The yield was 2.11 kg (9.33 mol, 55%) [1S-(1<a,3<b,5<a]-3-aminocarbonyl)-2-azabicyclo[3.1.0]hexane-2-carboxylic acid, 1,1-dimethylethyl ester (Formula H).

Example 35

Deprotection of [1S-(1<a,3<b,5<a)]-3-(aminocarbonyl)-2-azabicyclo[3.1.0]hexane-2-carboxylic acid, 1,1-dimethylethyl ester (Formula H) to form (1S,3S, 5S)-2-azabicyclo[3.1.0]hexane-3-carboxamide (Formula J)

A 100 ml, 2 necked flask equipped with a mechanical stirrer and a thermocouple was charged with [1S-(1<a,3<b, 5<a]-3-aminocarbonyl)-2-azabicyclo[3.1.0]hexane-2-carboxylic acid, 1,1-dimethylethyl ester (Formula H)(5.0 grams, 22.1 mmol) and THF (20 ml). HCl (2.5 M in EtOAc, 25 ml, 62.5 mmol) was then added to the suspension. The resulting solution was stirred at room temperature for 18 hours during which time precipitation was observed. Completion of the reaction was monitored by HPLC. Methyl t-butyl ether (MTBE ) (30 ml) was added to the suspension and stirring was continued for an additional 30 minutes. The suspension was then filtered under $N_2$ protection to produce a white solid that was washed with MTBE (20 ml). The solid was dried in an oven under reduced pressure for 48 hours to afford the hydrochloride salt of (1S,3S,5S)-2-azabicyclo[3.1.0]hexane-3-carboxamide (Formula J; 3.6 grams, 100%).

Example 35A

Alternative preparation of (5S)-5-aminocarbonyl-4, 5-dihydro-1H-pyrrole-1-carboxylic acid, 1-(1,1-dimethylethyl)ester (Formula IV)

A. Conversion of 4,5-dihydro-1H-pyrrole-1,5-dicarboxylic acid, 1-(1,1-dimethylethyl)

To a suspension of 10.4 g (25.86 mmol) of solid dicyclohexylamine (DCHA) salt in a mixture of 30 mL water, 40 mL of toluene and 10 mL MTBE were added 2.7 mL of 10N aq. NaOH (27 mmol) (excess of NaOH should be limited to 1.05 eq. or less). Upon stirring a biphasic mixture with clear layers resulted and all the solid dissolved Phases were split. The spent organic containing the 4,5-dihydro-1H-pyrrole-1,5-dicarboxylic acid, 1-(1,1-dimethylethyl) sodium salt was extracted with 4 mL water which was added to the initial aqueous phase. HPLC quantitation gave 12.55% (w/w) of "free olefin-acid" content in the aqueous or 96% recovery.

B. Generation of DMT-MM

To a solution of 2-Cl-4,6-diMeO-1,3,5-triazene (CDMT) (6.2 mg, 35 mmol; 1.5 eq.) in 70 mL of EtOAc kept in a room temperature water bath were added 4 mL (36.38 mmol) of neat N-methylmorpholine (MM). Solid 4-(4,6-dimethoxy-1, 3,5-triazin-2-yl)-4-methylmorpholinium chloride (DMT-MM) started to precipitate out. The suspension containing DMT-MM was stirred for 30 min at room temperature at which time it became a thick paste. The temperature rose from 23 to 28-29° C. during the reaction. The temperature of the reaction is kept down to minimize competing demethylation to form di-MeO—N morfolino-triazene (DMMT).

C. Conversion of the sodium salt of -4,5-dihydro-1H-pyrrole-1,5-dicarboxylic acid, 1-(1,1-dimethylethyl) into (5S)-5-aminocarbonyl-4,5-dihydro-1H-pyrrole-1-carboxylic acid, 1-(1, 1-dimethylethyl)ester IV To a solution of sodium salt of Part A sodium salt equivalent to 5 g (23.5 mmol) of free olefin-acid by HPLC quantitation (V=25 mL) was added solid $NH_4Cl$ (3.75 g, 70 mmol, 3 eq.) at which time pH dropped from 14 to 8.9. To this solution were added enough $NaH_2PO_4 \times H_2O$ to adjust pH to pH=6.20. Note: The amount of phosphate may vary depending on the initial excess of NaOH used to convert the DCHA salt into Na-salt. The buffered solution of sodium salt was run into a suspension to DMT-MM prepared as above in Part B.

The biphasic mixture was stirred at rt. for 4 h at which time the initial emulsion became a suspenion and some DMHT precipitated out. By HPLC the reaction was complete and neither activated DMT-ester nor acid were apparent in either phase.

Under the reaction conditions 12-15% by weight of 4,6-diMeO-1,3,5-triazene ether (DMT-ether) is also formed through a reaction of DMT-MM and DMHT. The suspension was filtered to remove 4,6-diMeO-1,3,5-triazene (DMHT) and the phases were split. The rich organic phase was washed with 2N aqueous $NaH_2PO_4 \times H_2O$ (2×25 mL) or until pH (aq.)<6 which implied that most N-methylmorpholine was removed from the organic. The phases were split and the rich organic was washed with 25 mL of brine.

Typically solution yield of the title compound IV is 87-90%; unreacted starting olefin-acid at 1-0%. The rich organic was rotoevaporated and azeotropically dried with fresh EtOAc (2×250 mL). The material partially crystallized. The mixture was dissolved in 8 mL of hot EtOAc and mixed with 10 mL of n-heptane. A solid started to come out. The suspension was stirred at 50° C. for 30 min and additional 10 mL of n-heptane were added. The suspension was stirred for 30 min at room temperature after having been removed from the heating bath and every 30 min two additional heptane charges are made and the suspension is stirred overnight at room temperature to complete crystallization. The solid is filtered and dried. Typical crystallization yield is close to 90%; the potency of the title compound IV is 90% and the DMT-ether accounts for the remaining 10% by weight.

The solid formed was found to be a true co-crystal of title compound IV and DMT-ether which gave a single sharp mp of 97.4° C. compared to amide's mp of 89.7° C. by DSC. The co-crystal form is more crystalline and more readily comes out of solution.

Example 35B

Preparation of dicyclohexyhamine salt of 4,5-dihydro-1H-pyrrole-1,5-dicarboxylic acid, 1-(1,1-dimethylethyl)

A. Preparation of the sodium salt of 4,5-dihydro-1H-pyrrole-1,5-dicarboxylic acid, 1-(1,1-dimethylethyl)

3 Volumes of ethanol were added to a toluene solution of 4,5-dihydro-1H-pyrrole-1.5-dicarboxylicacid, 1-(1,1-dimethylethyl) (about 15 wt % to 25 wt %) (1 g/mL). The solution was cooled to 0-5° C. To the solution was added slowly a 5N solution of NaOH-water (2 eqs) while maintaining temperature <5° C. (slightly exothermic). The reaction mixture was warmed to 20-25° C. and stirred until the reaction was completed.

4 Volumes of water were added to the reaction mixture and the reaction mixture was distilled under vacuum (bath temp. 40° C. ) to remove ethanol. To the residue was added 0.5 volume of toluene (0.865 g/mL) and the mixture was stirred for 10 minutes. Aqueous and organic layers formed. The aqueous layer containing the sodium salt was separated and used in Part B.

B. Preparation of dicyclohexylamine salt of 4,5-dihydro-1H-pyrrole-1,5-dicarboxylic acid, 1-(1,1-dimethylethyl)

1 Volume of MTBE (0.74 g/mL) was added to an aqueous solution of 4,5-dihydro-1H-pyrrole-1,5-dicarboxylic acid, 1-(1,1-dimethylethyl)-sodium salt. 0.2 Volume of heptane (0.684 g/mL) was added to the above solution and the resulting solution was cooled to 0-5° C. To the solution was added slowly 85% $H_3PO_4$ (1 g/mL) to bring the pH to ~2.5-3 while maintaining temperature <5° C. (slightly exothermic). The resulting layers were separated and to the organic layer containing the product was added 1 volume of 75% brine. The mixture was stirred for 10 minutes and the resulting layers were separated. The product was contained in the organic layer.

The organic solution was cooled to 0-5° C. and dicyclohexylamine (0.91 g/mL) was added slowly (slighley exothermic) while maintaining temperature <10° C. The reaction mixture was stirred at 0-5° C. for 3 hours. The solids were filtered out and washed with 0.5 volume of 1:1 MTBE/heptane. The resulting DCHA salt (1 g/mL) was dried and recovered.

Example 35C

Alternative preparation of [1S-(1<a,3<b,5<a)]-3-(aminocarbonyl)-2-azabicyclo[3.1.0]hexane-2-carboxylic acid, 1,1-dimethylethyl, ethyl ester (Formula H) (also referred to as syn-N-BOC-4,5-methanoproline)

A. Preparation of (s)-BOC-4,5-methanoproline ethyl ester

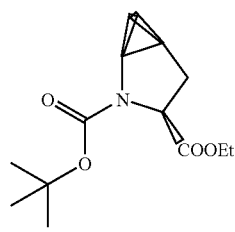

A flame-dried 3-necked flash (magnetic stirring) was charged with 2.2 g of 4,5-dihydro-1H-pyrrole-1,5-dicarboxylic acid, 1-(1,1-dimethylethyl),5-ethyl ester (2.20 g, 9.12 mmole, 1 eq) and 22 ml of dry toluene. The resulting solution was cooled to −30° and charged further dropwise with 16.58 ml (18.24 mmole) of diethyl zinc (1.1 m solution in toluene).

A solution of 2.66 ml (6.43 g, 36.47 mmole) of chloro iodomethane in 2.2 ml toluene was added dropwise while keeping the reaction temperature between −25° C. and −30° C. The reaction was kept at −20° C. for 16 hr. The reaction was then quenched with 22 ml of half-saturated bicarbonate solution and warmed to room temperature. A white precipitate formed which was filtered off over Hyflow (filter aid) and washed with toluene (ca 10 ml). The organic layer was separated from the biphasic filtrate and washed twice with water (11 ml each time). The organic layer was evaporated to dryness to give a yellowish oil (2.33 g) which was N-BOC-methanoproline ethyl ester (mixture of syn- and anti-(8:1) isomers).

The above procedure was used to make large quantities of the above mixture of isomers sufficient for use in the next stop. At 20-25° C., 3.40 kg of the N-BOC 4,5-methanoproline ethyl ester (mixture of syn- and anti-isomers) were vigorously stirred with 5.17 kg (66.59 gmol) 40.0% methyl amine (solution in water) under a nitrogen atmosphere.

After complete reaction, the mixture was diluted with 5.17 l water and 5.17 l MTBE and stirred for another 5 minutes before phase-split occurred. The organic layer was washed with 5.17 l water. The resulting organic layer was evaporated (vacuum, Tmax 40° C.) to constant weight.

A yield of 2.52 kg syn-N-Boc-4,5-methanoproline ethyl ester (9.85 mol, 74%) was obtained.

B. Preparation of s-BOC-4,5-methanoproline

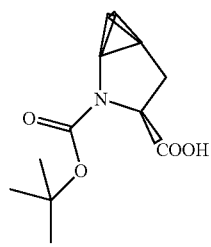

A solution of 2.57 kg syn-N-BOC 4,5-methanoproline ethylester (s-BOC-MPEE) in 10.28 l ethanol is prepared. To this solution is added at 20-28° C. a solution made of 0.51 kg lithium hydroxide hydrate in 5.07 l water. The reaction was performed under inert gas protection (nitrogen). The reaction mixture is stirred for 14 h at 20-25° C. (IPC). After complete reaction, the mixture evaporated at 40° C. (vacuum). The resulting oil was taken into 25.70 l water and 25.70 l MTBE and stirred for 30 min. The organic phase separated and the aqueous layer is again extracted with 12.85 l MTBE. To the aqueous phase are added 25.70 l MTBE and the pH of the mixture is adjusted to pH 2 by addition of 1 N HCl (ca. 12 l). The organic layer separated and the aqueous phase was re-extracted with 12.85 l MTBE. The combined organic layers from the previous step are evaporated to dryness to yield 1.88 kg syn-N-BOC 4,5-methanoproline (8.25 mol %, 82%).

C. Preparation of [1S-(1<a,3<b,5<a)]-3-(aminocarbonyl)-2-azabicyclo[3.1.0]hexane-2-carboxylic acid, 1,1-dimethylethyl ester

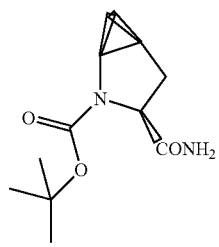

2.00 kg syn-N-BOC-4,5-methanoproline are dissolved in 40.00 l THF and cooled to −15° C. To this mixture is added 1.07 kg N-Methyl morpholine (P0). To the reaction mixture is charged 1.32 kg Isobutyl chloroformate in a way that the reaction temperature does not exceed −8° C. After complete addition the mixture is stirred for 30 min at −10° C. (P1, IPC 1). N-Methyl morpholine hydrochloride precipitates from the reaction mixture.

The reaction mixture is warmed to −5° C. and then purged via a gas inlet tube with ammonia (0.79 kg, theor. 5.00 eq.). Then the reaction mixture is warmed to 20-25° C. and stirred at this temperature for 4 h (P2, IPC 2). To the reaction mixture is added 40.00 l sat. brine. Then the pH of the mixture is adjusted to pH 4 to 4.5 by addition of sat.potassium bisulfate solution. Then the organic layer is separated and the aqueous phase is again extracted with 20.00 l MTBE. The combined organic layers are evaporated to dryness. The crude product is dissolved in 8.00 l butyl acetate at reflux temperature. Product precipitates at ca. 30° C. On start of crystallization the mixture is slowly treated with 20.00 l heptane and further stirred for another 2 h. The product is isolated by filtration. The filter cake is washed with two portions of cold butyl acetate/heptane (1:4), 1.6 l each, and twice with 2.00 l heptane, each and dried at 30-35° C. (vacuum) to yield 1.64 kg (7.22 mol, 82%) syn-N-BOC 4,5-methanoproline amide (s-BOC-MPA).

Example 36

BOC Protection of (<aS)-<a-amino-3-hydroxytricyclo[3.3.1.1$^{3,7}$]decane-1-acetic acid (Formula V) to form (<aS)-<a[[(1,1-dimethylethoxy) carbonyl] amino]-3-hydroxytricyclo[3.3.1.1$^{3,7}$]decane-1-acetic acid, (VI)

Formula VI Acid (<aS)-<a-amino-3-hydroxytricyclo[3.3.1.1$^{3,7}$]decane-1-acetic acid (Formula V) (469 grams, 2.08 moles) was dissolved in ice cold 1 N NaOH (5 liters, 5 moles, 2.4 equivalents) in a phase splitter equipped with a temperature probe and a pH probe. THF (2.5 liters) was added to the solution. Solid $Boc_2O$ was then added and the reaction mixture was stirred at ambient temperature for approximately 1 hour. EtOAc (4 liters) was then added with stirring and the resulting organic and aqueous layers were separated. The pH of the aqueous layer was adjusted to 7 with concentrated HCl. EtOAc (4 liters) was then added and additional HCl was added to lower the pH to approximately 1. The total volume of concentrated HCl added was 510 ml. The organic and aqueous layers were again separated and the aqueous layer was extracted with EtOAc (3×3 liters). The organic layers were then combined and washed with water (3 liters) and brine (3 liters). The washed organic layer was then dried with $Na_2SO_4$ and concentrated on a rotovap at room temperature until dryness. The yield was 542 grams of (<aS)-<a[[(1,1-dimethylethoxy)carbonyl]amino]-3-hydroxytricyclo[$3.3.1.1^{3,7}$]decane-1-acetic acid (Formula VI).

Example 37

Coupling Reaction to produce 3-aminocarbonyl-(<aS)-<a-(3-hydroxytricyclo[$3.3.1.1^{3,7}$]dec-1-yl)-<b-oxo-(1S,3S,5S)-2-azabicyclo[3.1.0]hexane -2-ethanecarbamic acid, 1,1-dimethylethyl ester (Formula K)

A 2 L three-necked flask equipped with a thermometer, a mechanical stirrer and a gas inlet was charged with (<aS)-<a[[(1,1-dimethylethoxy)carbonyl]amino]-3-hydroxytricyclo[$3.3.1.1^{3,7}$]decane-1-acetic acid (Formula VI) (50 grams, 153.8 mmol). THF (200 ml) was added and stirred to produce a clear solution. The solution was cooled to −6° C. in an acetone-dry ice-water bath. Methanesulfonyl chloride (Mes-Cl)(13.1 ml, 169 mmol, 1.1 equivalents) was then added as a single portion followed by diisopropylethylamine (94 ml, 539 mmol, 1.1 equivalents). The diisopropylethylamine was added slowly over a period of about 4 minutes to keep the internal temperature below 8° C. The reaction mixture was stirred at 0° C. until all acid was converted to mixed anhydride. (1S,3S,5S)-2-azabicyclo[3.1.0]hexane-3-carboxamide hydrochloride salt (32.5 grams, 200 mmol, 1.1 equivalents) and hydroxybenzotriazole (HOBT) (1.04 grams, 7.6 mmol, 0.05 equivalents) were then added in a single portion and the flask was removed from the cooling bath. The reaction mixture was stirred at room temperature for 2 hours and then left overnight at room temperature.

Example 38

BOC Protection of (<aS)-<a-amino-3-hydroxytricyclo[$3.3.1.1^{3,7}$]decane-1-acetic acid (Formula V) to form (<aS)-<a[[(1,1-dimethylethoxy)carbonyl]amino]-3-hydroxytricyclo[3.3.1.13,7]decane-1-acetic acid, 1,4-diazabicyclo[2.2.2]octane salt (Formula VIA)

Formula VIA (DABCO Salt)
1,4-Diazabicyclo[2.2.2]octane (DABCO) (15 g; 125.1 mmole) was charged into a solution of ca. 30 g (135 mmole) of Example 36 Formula VI acid in 300 ml of isopropyl acetate. Ethyl acetate (150 mL) was charged into the above reaction mixture (volume ratio of ethyl acetate: isopropyl acetate (150 mL/300 mL)). The reaction mixture was seeded with Formula VIA DABCO salt (200 mg). The reaction mixture was stirred vigorously at room temperature. Water (5 mL) was slowly charged to the reaction mixture and the reaction mixture stirred vigorously at room temperature to induce crystal formation after 15-20 minutes. The reaction mixture was stirred for 16 hours at room temperature and the reaction product was filtered in a Buchner funnel. The solids were washed with ethyl acetate at room temperature and dried at 50° C. in vacuo to give 47 g (79%) of the Formula VIA DABCO salt.

Example 39

Coupling Reaction to produce 3-aminocarbonyl-(<aS)-<a-(3-hydroxytricyclo[$3.3.1.1^{3,7}$]dec-1-yl)-<b-oxo-(1S,3S,5S)-2-azabicyclo[3.1.0]hexane-2-ethanecarbamic acid, 1,1-dimethylethyl ester (Formula K)

A 250 L three-necked flask equipped with a thermometer, a mechanical stirrer and a gas inlet was charged with (<aS)-<a[[(1,1-dimethylethoxy)carbonyl]amino]-3-hydroxytricyclo[$3.3.1.1^{3,7}$]decane-1-acetic acid, 1,4-diazabicyclo[2.2.2]octane salt (Formula VIA) (5 grams, 11.44 mmol) prepared in Example 38. THF (25 ml) was added and stirred to produce a slurry. The slurry was cooled to 0° C. in an ice-water bath. Methanesulfonyl chloride (Mes-Cl)(1.15 ml, 14.85 mmol, 1.3 equivalents) was then added as a single portion followed by diisopropylethylamine (94 ml, 40 mmol, 3.5 equivalents). The diisopropylethylamine was added slowly over a period of about 4 minutes to keep the internal temperature below 5° C. The reaction mixture was stirred at 0° C. for 10 minutes until all acid was converted to mixed anhydride. (1S,3S,5S)-2-azabicyclo[3.1.0]hexane-3-carboxamide hydrochloride salt (2.42 grams, 14.9 mmol, 1.3 equivalents) and hydroxybenzotriazole (HOBT) (77 mg, 0.57 mmol, 0.05 equivalents) were then added in a single portion and the flask was removed from the cooling bath. The reaction mixture was stirred at room temperature for 2 hours and then left overnight at room temperature.

Example 40

Dehydration and Hydrolysis to Produce 3-cyano-(<aS)-<a-(3-hydroxytricyclo[$3.3.1.1^{3,7}$]dec-1-yl)-<b-oxo-(1S,3S,5S)-2-azabicyclo[3.1.0]hexane-2-ethanecarbamic acid, 1,1-dimethylethyl ester (Formula L)

Pyridine (6 equivalents, 922 mmol, 74.6 ml) was added to the reaction mixture of Example 39 and the reaction mixture was cooled in a cooling bath to −8° C. Trifluoroacetic anhydride (TFAA) (4 equivalents, 616 mmol, 87 ml) was then added slowly over 6 minutes while keeping the temperature below 10° C. The reaction was stirred at 24° C. for 0.5 h and checked via HPLC (30 ml, 0.5 ml AcN, 0.5 ml $H_2O$) for the disappearance of Example 37 Compound K.

The reaction was then cooled in a cooling bath to approximately −3° C. NaOH (5 N, 6 equivalents, 0.925 mol, 185 ml) was added to the reaction over 10 minutes (aqueous pH=9.9) while maintaining the reaction temperature below 10° C. Aqueous $K_2CO_3$ (319 grams, 15 equivalents, dissolved in 510 ml $H_2O$) was added over 5 minutes (temperature=8° C., aq. pH 11.1). The reaction was allowed to run for 7 hours 40 minutes. The reaction was complete when all intermediates were hydrolyzed to penultimate as determined via HPLC (30 μl, 0.5 ml AcN, 0.5 ml $H_2O$).

EtOAc (500 ml) was then added to the reaction mixture and the resulting aqueous and organic layers were separated. The organic layer was washed with 500 ml buffer solution (2M $H_3PO_4$, 1M $NaH_2PO_4$). The temperature rose to 23° C. from 15° C.; addition time: 5 min., aq. V=560 ml pH=4.5, 32 mg product by HPLC; org V=1,080 ml. The organic was washed with a second 500 ml buffer solution; aq. V=780 ml, pH=2.5, 415 mg product by HPLC; organic V=800 ml, 1.02 v/v % pyridine. The organic was washed with 300 ml brine; aq. V=350 ml, pH=1.8, 20 mg produced by HPLC. The organic was washed with 130 ml sat. NaHCO$_3$ solution; aq. V=176 ml, pH=6.0, 780 mg product. The organic was washed with 300 ml half sat. brine; aq. V=330 ml, pH=5.2, 25 mg product; organic V=650 ml, pyridine 0.045 v/v %. 5 g Darco was added to the organic and stirred for 5 min, filtered through 50 g silica, washed with 4×25 ml EtOAc, organic V=750 ml, pyridine 0.04 v/v %.

The organic layer was then distilled to approximately 133 ml. The organic was stirred for 1 hour until the solution turned cloudy. 133 ml heptane was added over 15 min. and the slurry stirred overnight. 133 ml heptane was added overnight. The mixture was stirred violently for 20 minutes with mechanical stirring. The solids were filtered off and the cake was washed with 50 ml 5% EtOAc/heptane; 3.4 g product was found in 8.86 g crude after removal of solvents from the mother liquor. Dry product crystals were heated at 50° C. under vacuum overnight. 467 g product was obtained ~73%, 96.6 AP.

Example 41

Deprotection to produce (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) (Formula M)

3-cyano-(<aS)-<a-(3-hydroxytricyclo[3.3.1.1$^{3,7}$]dec-1-yl)-<b-oxo-(1S,3S,5S)-2-azabicyclo[3.1.0]hexane-2-ethanecarbamic acid, 1,1-dimethylethyl ester (Formula L)(5.0 grams, 12.04 mmoles) was charged to a three-necked flask equipped with a thermometer, a mechanical stirrer, and a gas inlet. EtOAc, approximately 45 to 50 ml, was added to achieve a clear solution. Concentrated HCl (3.00 ml, 37% w/w %, 36.14 mmoles, 3 equivalents) was added at room temperature and the reaction mixture was stirred until a solid was produced. Water (30 ml) was then added and the mixture was stirred for 1 to 2 minutes. This reaction mixture was transferred to a separatory funnel and the layers of the reaction mixture were allowed to separate into a clean phase split. The aqueous layer was adjusted to a lower pH of approximately 6 with 25% NaOH while maintaining the temperature below 25° C.

Salt exchange was then performed by addition of isopropyl alcohol (IPA; 2 to 3 ml) to the aqueous layer followed by addition of sodium benzoate (0.65 ml of a sodium benzoate solution prepared by dissolving 2.6 grams for sodium benzoate in 6.5 ml of water). The remaining sodium benzoate solution was then added in dropwise fashion via an addition funnel. The resulting reaction mixture was stirred at room temperature for 16 to 24 hours. Solids in the reaction mixture were then filtered on a Buchner funnel and washed with water until the solid gave a negative test for Cl— with AgNO$_3$. The solids were then washed with heptane (10 ml) to drive off the water, air dried on the funnel, an dried in a vacuum oven at 35° C. until KF≦5%. Yield was 79%, 4.1 grams.

Example 42

Deprotection of L

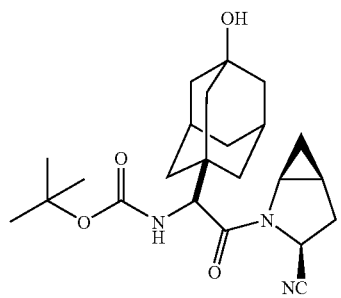

L to produce free base M'

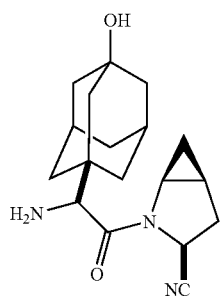

M' and its monohydrate M"

Example 40 compound (L) (300 g, 0.723 mol, potency of 90.6%), methylene chloride (3 L), methanol (288 ml, 7.23 mol) and concentrated (36%) hydrochloric acid (288 ml, 7.23 mol) were charged to a 3-neck 12 L flask equipped with mechanical stirrer, temperature probe and N$_2$ gas inlet. Reaction occurred while maintaining reaction temperature within the range from about 20 to about 25° C. The reaction mixture was stirred for 18 hours, split into 2 phases and the top aqueous layer was collected. To the aqueous layer was added methylene chloride (6 L), and water (720 ml), and 5N NaOH (600 ml) was added dropwise to adjust pH to 9.0~10.5.

The organic phase containing the hydrochloric salt

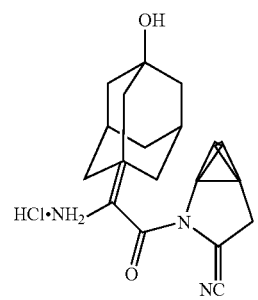

(identified by HPLC) (Formula L') was treated with methylene chloride (6 L) and water (720 ml), and 5N sodium hydroxide solution (~600 ml) was added dropwise while maintaining reaction temperature between 20 and 25° C. to adjust pH between 9 and 10.5. NaCl (120 g) was added and the mixture agitated for 20 min. to form a phase split. The organic layer (6.2 L) was collected (contained ~174 g of compound M') and the aqueous layer (1.75 L) was discarded (contained 6.5 g compound M').

The organic layer was washed with 1% $NH_4Cl$ brine solution (450 ml). (1% $NH_4Cl$ brine solution contained 1 g $NH_4Cl$, 25 g NaCl and 74 g $H_2O$). From the resulting phase split 6.0 L organic layer was recovered (contained ~176 g compound M' in solution) and the aqueous layer (0.45 L) containing 1.4 g compound M' (~0.4%) was discarded.

Ethyl acetate (~4 L) was added to the organic layer while $CH_2Cl_2$ was distilled off at 25° C./50 mm Hg. Distillation was discontinued when a final volume of 2.5 L was reached. The organic layer was polish filtered to remove solid NaCl and was concentrated to ~1 Kg (~170 g of compound M' in 1 L ethyl acetate) GC analysis: DCM<0.1%. Water (17 ml) was added dropwise and after 10 min. crystallization began. 17 ml of water was added and the resulting slurry was agitated for 30 min, filtered, the cake washed with ethyl acetate and dried at room temperature under vacuum to give 186 g of monohydrate compound M", yield 81%.

What is claimed is:

1. A compound of the structure of Formula IA:

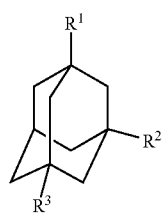

IA or a pharmaceutically acceptable salt thereof, wherein $R^1$ is OH;

$R^2$ is selected from the group consisting of —C(=O)—$COR^4$, —$C(X)_n$—$COR^4$ and

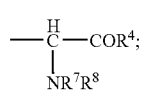

wherein

X is a halogen;

n is 2;

$R^4$ is selected from the group consisting of O-alkyl, $NH_2$ and OH; and $R^7$ and $R^8$ are each selected from the group consisting of H and $COOR^9$, wherein $R^9$ is alkyl; and $R^3$ selected from the group consisting of H or OH.

2. The compound of claim 1 of the structure of Formula I,

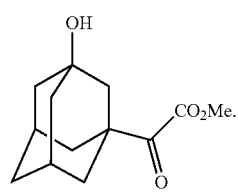

I

3. The compound of claim 1 of the structure of Formula II,

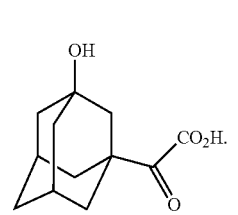

II

4. The compound of claim 1 of the structure of Formula V,

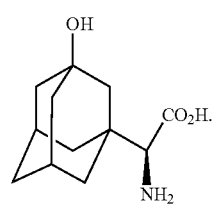

V

5. The compound of claim 1 of the structure of Formula VI,
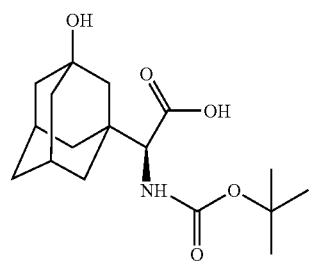
or its DABCO salt VIA
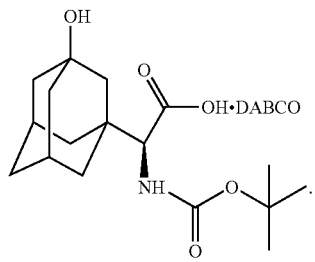
6. The compound of claim 1 of the structure of Formula VIII,
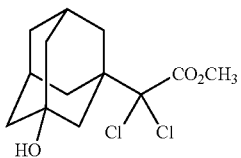
or the compound of the structure of Formula IX
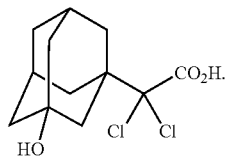
\* \* \* \* \*